US006541486B1

(12) United States Patent
Bitler et al.

(10) Patent No.: US 6,541,486 B1
(45) Date of Patent: Apr. 1, 2003

(54) BIS-BENZIMIDAZOLE COMPOUNDS AND ANALOGS THEREOF FOR INHIBITING CELL DEATH

(75) Inventors: Catherine M. Bitler, Menlo Park, CA (US); Paul L. Wood, Morgan Hill, CA (US); Duran T. Anstine, Nampa, ID (US); Anke Meyer-Franke, Menlo Park, CA (US); Qi Zhao, Fremont, CA (US); Mohamed A. Khan, Sunnyvale, CA (US)

(73) Assignee: Elan Pharma International Ltd., Dublin (IE)

( * ) Notice: Subject to any disclaimer, the term of this patent is extended or adjusted under 35 U.S.C. 154(b) by 0 days.

(21) Appl. No.: 09/587,043

(22) Filed: Jun. 2, 2000

Related U.S. Application Data
(60) Provisional application No. 60/137,618, filed on Jun. 4, 1999, provisional application No. 60/138,855, filed on Jun. 11, 1999, and provisional application No. 60/168,256, filed on Nov. 30, 1999.

(51) Int. Cl.$^7$ .................. A61K 31/4184; A61K 31/437; C07D 471/04; C07D 487/04

(52) U.S. Cl. ................. 514/303; 514/394; 546/118; 548/305.7

(58) Field of Search .................. 548/305.7; 514/394, 514/303; 546/118

(56) References Cited

U.S. PATENT DOCUMENTS

| | | | |
|---|---|---|---|
| 3,105,837 A | 10/1963 | Ursprung | |
| 3,337,578 A | 8/1967 | Bader et al. | |
| 3,337,579 A | 8/1967 | Ursprung | |
| 3,808,005 A | 4/1974 | Willems et al. | |
| 4,064,136 A | 12/1977 | Loew et al. | |
| 4,213,994 A | 7/1980 | Gebert et al. | |
| 4,324,794 A | 4/1982 | Tidwell et al. | |
| 4,835,085 A | 5/1989 | Bauer | |
| 4,940,723 A | 7/1990 | Tidwell et al. | |
| 4,981,613 A | 1/1991 | Okazaki et al. | |
| 5,147,863 A | 9/1992 | Matthews et al. | |
| 5,387,600 A | 2/1995 | Aikawa et al. | |
| 5,428,051 A | 6/1995 | Tidwell et al. | |
| 5,578,631 A | 11/1996 | Tidwell et al. | |
| 5,585,091 A | 12/1996 | Pelzer et al. | |
| 5,693,515 A | 12/1997 | Clark et al. | |
| 5,961,960 A | * 10/1999 | Dilk et al. | 424/59 |

FOREIGN PATENT DOCUMENTS

| | | |
|---|---|---|
| DE | 21 58 294 | 5/1972 |
| JP | 05287562 A2 | 11/1993 |
| JP | 05291729 A2 | 11/1993 |
| WO | WO 95/19772 | 7/1995 |
| WO | WO 98/22619 | 5/1998 |

OTHER PUBLICATIONS

Roderick et al., CA 77:70742, 1972.*
Cakir et al., CA 110:20835, 1989.*
Kuecuekbay et al., CA 124:232388, 1996.*
Cakir, B., et al., "bis–Benzothiazole derivatives and their antifungal activities" *Gazi Univ. Eczacilik Fak. Derg.* 4(2):143–149 (1987) abstract only.
Cakir, B., et al., "Benzimidazole derivatives: bis–benzimidazoles and their antifungal activities" *Gazi Univ. Eczacilik Fak. Derg.* 5(1):71–7 (1988) abstract only.
De Meo, M., et al., "Evaluation of the Mutagenic and Genotoxic Activities of 48 Nitroimidazoles and Related Imidazole Derivatives by the Ames Test and the SOS Chromotest" *Environmental and Molecular Mutagenesis* 19:167–181 (1992).
Ferrania Societa per Azioni, "Photographic emulsions" *Chemical Abstracts* 65:abstract #203a (1966).
Goin, C.J. and Mayer, V.W., "Induction of chromosome loss in Saccharomyces cerevisiae strain D61.M by selected benzimidazole compounds" *Mutat. Res.* 343(4):185–199 (1995) abstract only.
Gunes, H.S. and Cosar G., "2–Alkyl substituted benzimidazole derivatives and their antifungal activities" *J. Fac. Phar. Gazi Univ.* 13(1):57–64 (1996) abstract only.
Joseph, M., et al., "Synthesis of and Novel Reactions with Bis[imidazol–2–yl]nitromethane" *Communications* Jul.:459–461 (1977).
Kaliszan, R., et al., "Studies on quantitative relationships between the structure and in vitro tuberculostatic potency of 2–cyanomethylbenzimidazole derivatives" *Pol. J. Pharmacol. Pharm.* 30(4):585–591 (1978) abstract only.
Kozhokaru, A.F., et al., "Effect of the derivatives of tetrachlorotrifluoromehtylbenzimidazole on bilayer lipid membranes" *Deposited document Viniti 800–83* pp. 1–18 (1983) abstract only.
Mikhnovs'ka, N.D., et al., "Effect of some benzimidazole derivatives on type A influenza virus" *Mikrobiol. Zh.* 30(1):62–65 (1968) abstract only.
Noyanalpan, N. and Isikdag, I., "Study on the synthesis of 2–substituted–benzimidazole derivatives and their qualititative analyses and structure–activity relationships" *Doga Bilim Derg.* 9(2):183–193 (1985) abstract only.

(List continued on next page.)

*Primary Examiner*—Laura L. Stockton
(74) *Attorney, Agent, or Firm*—LeeAnn Gorthey; Perkins Coie LLP

(57) ABSTRACT

Compounds, pharmaceutical compositions, and methods of use are described which are effective in inhibiting cell death, particularly apoptotic cell death. The compositions may be used for prevention and treatment of injuries associated with cell death, including ischemia, such as results from stroke or myocardial infarction, trauma, neurodegeneration, and inflammation.

19 Claims, 3 Drawing Sheets

OTHER PUBLICATIONS

Pujar, M.A., et al., Screening of Schiff base and Benzamidazole Derivatives for their Antibacterial Activity *Indian Journal of Microbiol.* 27:(1–4):75–77 (1987).

Revankar, G.R. and Siddappa, S., "Synthesis of bis(4–azabenzimidazoles)" *Chemical Abstracts* 61: abstract #652h (1964).

Schuetze, W., "Synthesis of some 2,2'–dibenzimidazolyl–, 2,2'–diimidazolyl–, and diimidazolylbenzene compounds" *Chemical Abstracts* 61:abstract #8295c (1964).

van der Stelt, C., et al., "Synthesis and pharmaceutical properties of a series of α,α–diaryl–1H–imidazole–2–methanol derivatives" *Eur. J. Med. Chem.* 13(3):251–258 (1978).

Vertinskaya, M.K. and Govorova, S.V., "Possible application of biochemical models for screening anthelmintics" *Tr. Gel'mintol. Lab* 32:20–24 (1984).

\* cited by examiner

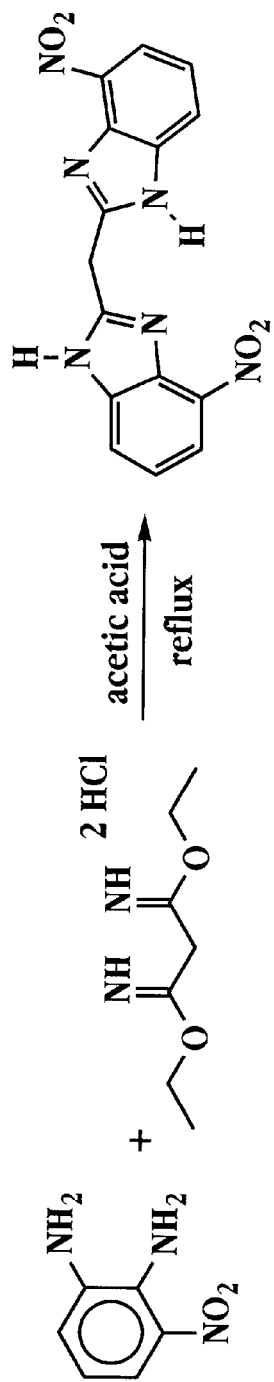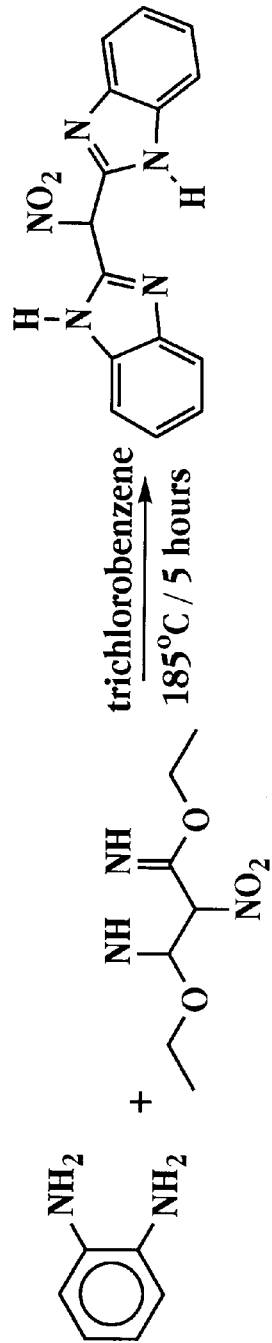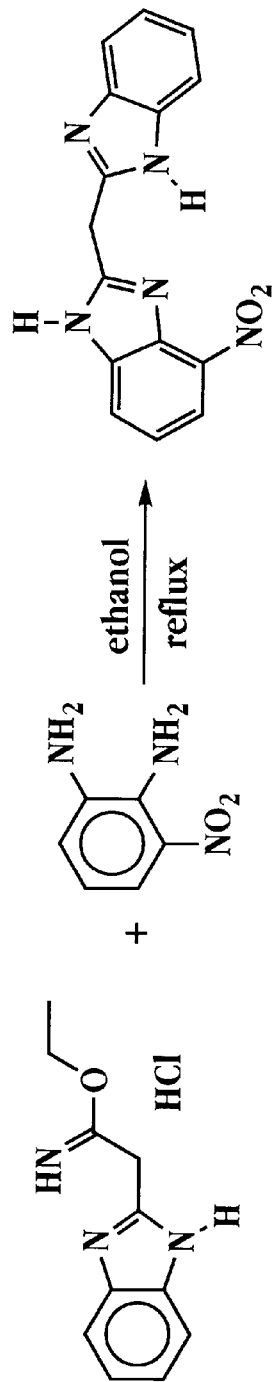
Fig. 1A
Fig. 1B
Fig. 1C

BIS-BENZIMIDAZOLE COMPOUNDS AND ANALOGS THEREOF FOR INHIBITING CELL DEATH

This application claims priority to U.S. provisional applications having Ser. Nos. 60/137,618, filed Jun. 4, 1999; 60/138,855, filed Jun. 11, 1999; and 60/168,256, filed Nov. 30, 1999, each of which is hereby incorporated by reference in its entirety.

FIELD OF THE INVENTION

The present invention relates to compounds and methods for inhibiting cell death, such as neuronal or myocardial cell death. The compounds and pharmaceutical compositions thereof are particularly effective in inhibiting apoptotic cell death, and thus may be used to protect cells from cell death associated with ischemia, trauma, neurodegeneration, and inflammation.

REFERENCES

Barres et al., *Neuron* 1:791–803 (1988).
Barres et al., *Cell* 70:31–46 (1992).
Barres et al., *Development* 118:283–295 (1993a).
Batistatou et al., *J. Cell Biol.* 122:523–532 (1993).
Brewer et al., *J. Neurosci. Res.* 35:567–576 (1993).
Busciglio et al., *Nature* 378:776–779 (1995).
Ghosh et al., *Science* 263:1618–1623 (1994).
Goldberg et al., *Nat. Genetic* 13:442–449 (1996).
Greenlund et al., *Neuron* 14:373–376 (1995).
Harnisch, U.S. Pat. No. 3,985,763 (1976).
Hinton et al., *Arch. Ophthalmol.* 116:203–209 (1998).
Kim et al., *Science* 277:373–376 (1997).
Kirino, T., *Brain Res.* 239:57–69 (1982).
Koizumi et al., *Jpn. J. Stroke* 8:1–8 (1986).
Laquis et al., *Brain Res.* 784:100–104 (1998).
Lazdins et al., *J. Exp. Med.* 185:81–90 (1997).
Liston et al., *Nature* 379:349–353 (1996).
MacManus et al., *Neurosci. Lett.* 164:389–392 (1993).
Meyer-Franke et al., *Neuron* 15:805–819 (1995).
Mosmann et al., *J. Immunol. Meth.* 65:55–63 (1983).
Nickells, R. W., *J. Glaucoma* 5(5):345–356 (1996).
Pulsinelli et al., *Stroke* 10:267–272 (1979).
Schwartz et al., *Proc. Natl. Acad. Sci. USA* 90 (3):980–984 (1993).
Tamura et al., *J. Cereb. Blood Flow Metab.* 1:53 (1981).
Vermes et al., *J. Immunol. Meth.* 184:39–51 (1995).
Vitale et al., *Histochemisty* 100:223–229 (1993).
Walton et al., *Neuroreport* 8(18):3871–3875 (1997).
Wyllie et al., *J. Pathol.* 142:67–77 (1984).
Zhao et al., *Brain Res.* 649:253–259 (1994).

BACKGROUND OF THE INVENTION

Apoptosis has been associated with ischemic injury, such as typically occurs in cases of stroke, myocardial infarction, and reperfusion injury (Walton et al., 1997; MacManus et al., 1993). Apoptosis is also associated with immunoreactive and immunodegenerative states and a variety of neurodegenerative disorders. Recent studies on the mechanism of retinal ganglion cell death in experimental glaucoma also indicate that the cells die by apoptosis (Nickells, 1996; Garcia-Valenzuela et al., 1995; Laquis et al., 1998).

Apoptosis is a programmed cell death, occurring in normally functioning human and animal cells when age or state of cell health and condition dictates. It is an active process requiring metabolic activity by the dying cell, and is often characterized by cleavage of the DNA into fragments that give a so called laddering pattern on gels. Cells that die by apoptosis do not usually elicit the inflammatory responses that are associated with necrosis, a passive process in which collapse of internal homeostasis leads to cellular dissolution.

Apoptosis can have particularly devastating consequences when it occurs pathologically in cells that do not normally regenerate, such as neurons. Because such cells are not replaced when they die, their loss can lead to debilitating and sometimes fatal dysfunction of the affected organ.

Various drug strategies have been proposed for treatment of stroke and other neuronal conditions related to ischemia. To date, however, these drugs have been either relatively ineffective or effective only at dosage levels where undesired side effects are observed. For example, anti-coagulants, such as heparin, antivasoconstriction agents, such as flunarazine, excitatory neurotransmitter antagonists, such as MK-801 and AP7, and anti-edemic compounds have shown mixed results, with no clear benefits to outweigh a variety of side effects, including neurotoxicity or increased susceptibility to infection. Verapamil and related compounds, which prevent calcium entry into smooth and striated muscles, appear to be effective only at high drug concentrations, where serious cardiotoxicity effects may ensue. Increased cerebral edema has been observed as a side effect in treatment with dihydropyridines, such as nimodipine. Benzothiazepines, as exemplified by diltiazem, have shown moderate protective effects, but these drugs also appear to cause undesired side effects, such as hypotension, which may be inimical to treatment.

SUMMARY OF THE INVENTION

In one aspect, the invention provides a pharmaceutical composition, useful for inhibiting cell death, which comprises an effective amount of a compound of formula I, or a pharmaceutically acceptable salt thereof, in a pharmaceutically acceptable carrier.

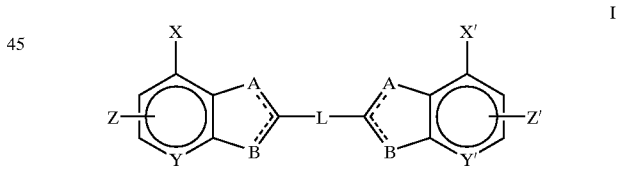

In formula I, X, X', Z and Z' are independently selected from the group consisting of hydrogen, alkyl, alkoxy, cyano, carboxylic acid or ester, sulfonic acid or ester, amino, alkylamino, nitro, and halogen. The linker L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate. The moiety A═══B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen, and where A═══B groups on opposing sides of the linker L may be the same or different. The groups Y and Y' are independently selected from carbon and nitrogen.

In selected embodiments, the linker L is $CH_2$, $CHCH_3$, or carbonyl, and is preferably $CH_2$. In further embodiments, in which A===B represents a three-atom linkage effective to form an imidazole ring fused to the adjacent six-membered ring, $NR^1$ is preferably NH, $NCH_3$, or $NCH_2C_6H_5$ (N-benzyl). Y and Y' are preferably carbon.

In further embodiments, X, X', Z and Z' are independently selected from hydrogen, alkyl, carboxylic acid or ester, amino, nitro, chloro, and fluoro. Preferably, at least one of X and X' is amino or nitro, and Z and Z' are independently selected from hydrogen, carboxylic acid, chloro, and fluoro. Not included are compositions in which, in Formula I, L is $CH_2$, Y is carbon, A===B represents a three-atom linkage effective to form an imidazole or pyrrole ring, X, X' and $R^1$ are hydrogen, and Z and Z' are each selected from hydrogen, nitro, amino, or halogen. However, methods of administering these compositions to inhibit cell death, as described below, are included in the invention.

Alternatively, the pharmaceutical compositions of the invention may comprise an effective amount of a compound of formula II, or a pharmaceutically acceptable salt thereof, in a pharmaceutically acceptable carrier.

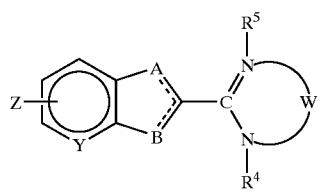

II

In formula II, L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate. $R^4$ is selected from hydrogen, alkyl, aryl, and aralkyl; and $R^5$ is selected from an electron pair, hydrogen, alkyl, aryl, and aralkyl. It is understood that when $R^5$ is not an electron pair, the compound has a positive charge (e.g. compound SNX-980). L is preferably $CR^2R^3$, where $R^2$ and $R^3$ are selected independently from hydrogen and lower alkyl.

As in formula I, A===B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen; and Y is carbon or nitrogen.

The group W represents a two- to four-carbon alkyl chain linking the two depicted nitrogen atoms to form a five- to seven-membered heterocyclic ring. Each carbon atom of the alkyl chain is unsubstituted or substituted with one or two lower alkyl groups or a hydroxyl group. Preferably, each carbon atom of the alkyl chain is unsubstituted or methyl substituted.

Z represents one or more substituents on the aryl ring containing Y, independently selected from the group consisting of hydrogen, alkyl, alkoxy, cyano, carboxylic acid or ester, sulfonic acid or ester, amino, nitro, and halogen. Preferably, Z is selected from hydrogen, methyl, amino, nitro, chloro, and fluoro.

In selected embodiments, A===B represents a three-atom linkage effective to form an imidazole ring fused to the adjacent six-membered ring, and Y and Y' are carbon. In further embodiments, $R^4$ is selected from hydrogen, lower alkyl, and benzyl, and $R^5$ is an electron pair.

Alternatively, the pharmaceutical compositions may comprise an effective amount of a compound of formula III, or a pharmaceutically acceptable salt thereof, in a pharmaceutically acceptable carrier.

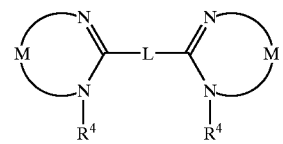

III

In formula III, L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate; each $R^4$ is independently selected from hydrogen, alkyl, aryl, and aralkyl; and M is —$CR^6R^7$—$CR^8R^9$— or —$CR^6$=$CR^8$—, where $R^6$—$R^9$ are independently selected from hydrogen and lower alkyl.

In selected embodiments, L is $CH_2$, $CHNH_2$, $CHNO_2$, carbonyl, or a direct bond. In further embodiments, $R^4$ is hydrogen or lower alkyl. In one embodiment, M is —$CR^6$=$CR^8$—, and $R^6$ and $R^8$ are independently hydrogen or methyl.

In a further embodiment, the pharmaceutical compositions comprise an effective amount of a compound of formula IV, or a pharmaceutically acceptable salt thereof, in a pharmaceutically acceptable carrier.

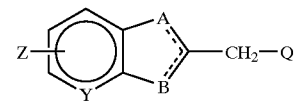

IV

In formula IV, as above, A===B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen, and Y is carbon or nitrogen. Z represents one or more substituents on the aryl ring containing Y, independently selected from the group consisting of hydrogen, alkyl, alkoxy, cyano, carboxylic acid or ester, sulfonic acid or ester, amino, nitro, and halogen. Q is selected from nitro and 2-pyridyl. Preferably, Y is carbon, and A===B represents a three-atom linkage effective to form an imidazole ring fused to the adjacent six-membered ring. In selected embodiments, Z is hydrogen.

In another aspect, the invention provides a method of inhibiting cell death. In accordance with the method, an effective amount of a compound of formula I, or a pharmaceutically acceptable salt thereof, in a pharmaceutically acceptable carrier, is administered to a subject in need of such treatment.

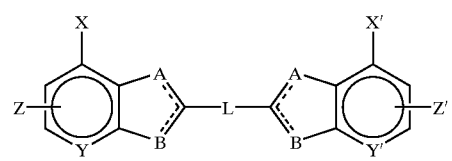

I

In formula I, as described above, X, X', Z and Z' are independently selected from the group consisting of hydrogen, alkyl, alkoxy, cyano, carboxylic acid or ester, sulfonic acid or ester, amino, alkylamino, nitro, and halogen; L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate; A===B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen, and where A===B groups on opposing sides of the linker L may be the same or different; and Y and Y' are independently selected from carbon and nitrogen.

In selected embodiments, the linker L is $CH_2$, $CHCH_3$, or carbonyl, and is preferably $CH_2$. In further embodiments, in which A===B represents a three-atom linkage effective to form an imidazole ring fused to the adjacent six-membered ring, $NR^1$ is preferably NH, $NCH_3$, or $NCH_2C_6H_5$ (N-benzyl). Y and Y' are preferably carbon.

In further embodiments, X, X', Z and Z' are independently selected from hydrogen, alkyl, carboxylic acid or ester, amino, nitro, chloro, and fluoro. Preferably, at least one of X and X' is amino or nitro, and Z and Z' are independently selected from hydrogen, carboxylic acid, chloro, and fluoro.

Alternatively, the method of the invention comprises administering an effective amount of a compound of formula II, or a pharmaceutically acceptable salt thereof, in a pharmaceutically acceptable carrier.

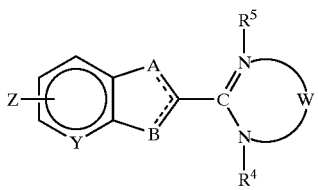

II

In formula II, as described above, L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate. $R^4$ is selected from hydrogen, alkyl, aryl, and aralkyl; and $R^5$ is selected from an electron pair, hydrogen, alkyl, aryl, and aralkyl. It is understood that when $R^5$ is not an electron pair, the compound has a positive charge (e.g. compound SNX-980). L is preferably $CR^2R^3$, where $R^2$ and $R^3$ are selected independently from hydrogen and lower alkyl.

A===B. represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen; Y is carbon or nitrogen.

W represents a two- to four-carbon alkyl chain linking the two depicted nitrogen atoms to form a five- to seven-membered heterocyclic ring. Each carbon atom of the alkyl chain is unsubstituted or substituted with one or two lower alkyl groups or a hydroxyl group. Preferably, each carbon atom of the alkyl chain is unsubstituted or methyl substituted.

Z represents one or more substituents on the aryl ring containing Y, independently selected from the group consisting of hydrogen, alkyl, alkoxy, cyano, carboxylic acid or ester, sulfonic acid or ester, amino, nitro, and halogen. Selected embodiments of the compounds of formula II which may be employed in the method are described above.

Alternatively, the method of the invention comprises administering an effective amount of a compound of formula III, or a pharmaceutically acceptable salt thereof, in a pharmaceutically acceptable carrier.

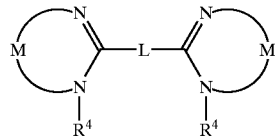

III

In formula III, L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate; each $R^4$ is independently selected from hydrogen, alkyl, aryl, and aralkyl; and M is —$CR^6R^7$—$CR^8R^9$— or —$CR^6$=$CR^8$—, where $R^6$—$R^9$ are independently selected from hydrogen and alkyl. Selected embodiments of the compounds of formula III which may be employed in the method are described above.

In a further embodiments, the method of the invention comprises administering an effective amount of a compound of formula IV, or a pharmaceutically acceptable salt thereof, in a pharmaceutically acceptable carrier.

IV

In formula IV, A===B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen; Y is carbon or nitrogen; Z represents one or more substituents on the aryl ring containing Y, independently selected from the group consisting of hydrogen, alkyl, alkoxy, cyano, carboxylic acid or ester, sulfonic acid or ester, amino, nitro, and halogen; and Q is selected from the group consisting of hydrogen, nitro, cyano, and 2-pyridyl. Selected embodiments of the compounds of formula IV which may be employed in the method are described above.

In one embodiment of the present method, the cell death being treated or prevented is apoptotic neuronal cell death, such as that associated with stroke, ischemia, neurodegeneration, trauma, an autoimmune response, or inflammation. In another embodiment, the cell death is associated with myocardial damage, such as myocardial infarction and the resulting ischemia, hypoxia and subsequent reperfusion in the affected area, or myocardial damage resulting from therapeutic intervention, e.g. coronary arterial bypass graft (CABG) or percutaneous transluminal coronary angioplasty (PTCA; "balloon" angioplasty).

In a further embodiment of the method, the compounds of formulas I–IV are administered in combination with an anti-hypertensive agent, an antibiotic, an inmmunomodulator, or an anti-inflammatory agent.

Also included within the invention are certain methylenebis(benzimidazole) compounds of formula I above, where L is $CH_2$, Y and Y' are carbon, and A===B represents a three-atom linkage effective to form an pyrrole ring fused to the adjacent-six-membered ring, and pharmaceutically acceptable salts thereof. The compounds are represented by structure Ia, below, where Z' represents a 4' or 5' substituent on the rightmost-depicted ring, and each of Z and Z' is selected from the group consisting of hydrogen, chloro, fluoro, carboxy, and methyl.

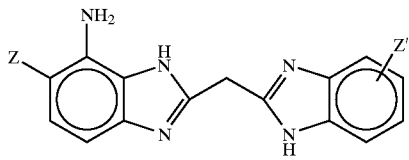

Ia

These compounds include the 4-amino substituted compounds:
- 2-(benzimidazol-2'-yl)methyl-4-amino benzimidazole (designated herein as SNX 912);
- 2-(5'-chlorobenzimidazol-2'-yl)methyl-4-amino benzimidazole (designated herein as SNX 923);
- 2-(benzimidazol-2'-yl)methyl-4-amino-5-chloro benzimidazole (designated herein as SNX 947);
- 2-(4'-fluorobenzimidazol-2'-yl)methyl-4-amino benzimidazole (designated herein as SNX 940);
- 2-(5'-fluorobenzimidazol-2'-yl)methyl-4-amino benzimidazole (designated herein as SNX 942);
- 2-(5'-carboxybenzimidazol-2'-yl)methyl-4-amino benzimidazole (designated herein as SNX 977); and
- 2-(4'-methylbenzimidazol-2'-yl)methyl-4-amino benzimidazole (designated herein as SNX 944).

Compounds of formula I also forming part of the invention include the 4-nitro substituted compounds 2-(benzimidazol-2'-yl)methyl-4-nitro-5-chloro benzimidazole (designated herein as SNX 937) and 2-(4'-nitro-5'-chlorobenzimidazol-2'-yl)methyl-4-nitro-5-chloro benzimidazole (designated herein as SNX 934), and the keto-linked compounds 2-(2-indolylcarbonyl)benzimidazole (designated herein as SNX 1772) and 2,2-carbonylbisbenzimidazole (designated herein as SNX 1719).

Also within the invention are selected compounds of formula II above, represented by structure IIa:

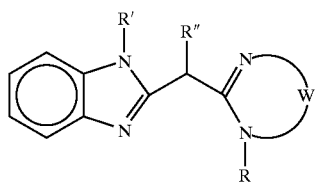

IIa where each of R, R' and R" is selected from hydrogen and methyl, and W represents a two- to four-carbon alkyl chain linking the two attached nitrogen atoms to form a five- to seven-membered heterocyclic ring. Each carbon atom of the alkyl chain is unsubstituted or substituted with one or two lower alkyl groups or a hydroxyl group. Preferably, each carbon atom of the alkyl chain is unsubstituted or methyl substituted. These include the compounds:
- 2-(3,4,5,6-tetrahydro-5-hydroxypyrimidin-2-yl)methyl benzimidazole (designated herein as SNX-1817);
- 2-(3,4,5,6-tetrahydropyrimidin-2-yl)methyl benzimidazole (designated herein as SNX-1818);
- 2-(4,5,6,7-tetrahydro-1,3-diazepin-2-yl)methyl benzimidazole (designated herein s SNX-1819); and
- 1-methyl-2-[(1-methyl-4,5-dihydro-imidazol-2-yl)ethyl benzimidazole (designated herein as SNX-1771).

Also included within the invention is a compound of formula II above, 2-(1,3-dimethyl-4,5-dihydro-1H-imidazol-2-ylmethyl)-1H-benzimidazole, designated herein as SNX 980.

These and other objects and features of the invention will become more fully apparent when the following detailed description of the invention is read in conjunction with the accompanying drawings.

BRIEF DESCRIPTION OF THE DRAWINGS

FIGS. 1A–1C illustrate synthetic methods for preparing compounds of the invention;

DETAILED DESCRIPTION OF THE INVENTION

I. Definitions

Figure 2:
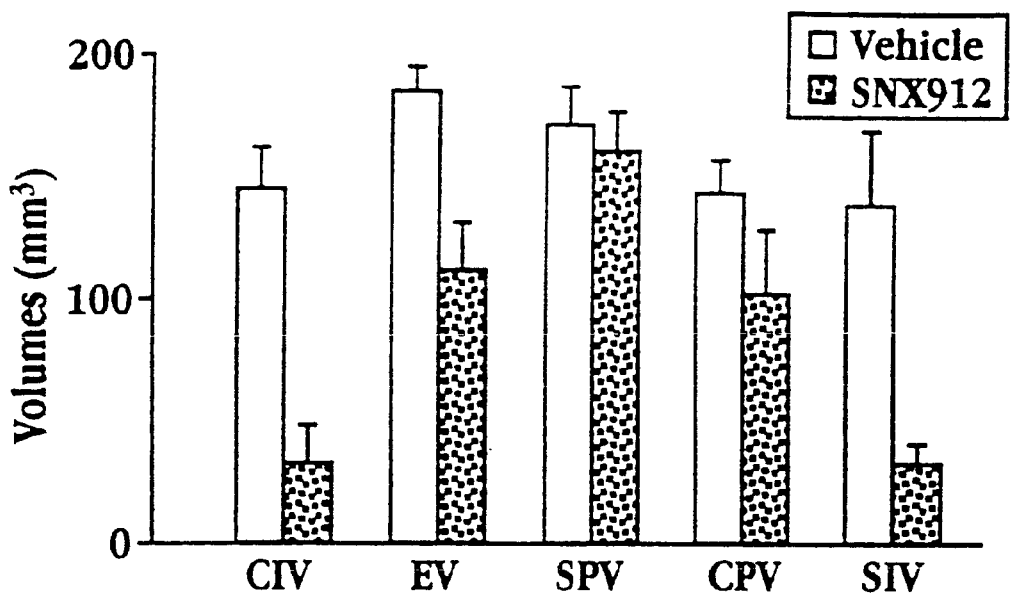
FIG. 2 shows the effect of ICV (intracerebroventricular) administration of SNX 912 on ischemic volume and infarct volume in the MCAO in vivo stroke model (CIV=cortical infarct volume; EV=edema; SPV=subcortical penumbra; CPV=cortical penumbra; SIV=subcortical infarct volume)

The terms below have the following meanings unless indicated otherwise.

"Alkyl" refers to a fully saturated acyclic monovalent radical containing carbon and hydrogen, which may be branched or a straight chain. Examples of alkyl groups are methyl, ethyl, n-butyl, n-heptyl, and isopropyl. "Lower alkyl", a subset of this class, refers to alkyl having one to six carbon atoms, and more preferably one to four carbon atoms.

"Aryl" refers to a substituted or unsubstituted monovalent aromatic radical having a single ring (e.g., benzene) or two or more condensed rings (e.g., naphthyl). Single ring aryl groups are generally preferred. Included are heterocyclic aromatic rings having one or more nitrogen, oxygen, or sulfur atoms in the ring, such as furyl, pyrrole, pyridyl, and indole. Carbocyclic aryl groups are generally preferred. By "substituted" is meant that one or more ring hydrogens in the aryl group is replaced with a non-hydrogen group, preferably selected from halogen, methyl, methoxy, hydroxyl, nitro, cyano, amino, methylamino, dimethylamino, carboxylic acid or ester, and sulfonic acid or ester. Unsubstituted groups or groups substituted with lower alkyl are generally preferred.

"Aralkyl" refers to a monovalent alkyl radical substituted with an aryl group, as defined above, e.g. a benzyl group (—$CH_2C_6H_5$).

An "aliphatic" compound is an acyclic or cyclic (alicyclic), saturated or unsaturated carbon compound, excluding aromatic compounds.

A "pharmaceutically acceptable salt" of a compound described herein refers to the compound in protonated form with one or more anionic counterions such as chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like. Hydrochloride salts are a preferred group.

II. Cell Death Inhibiting Compositions

The invention provides pharmaceutical compositions which are effective as inhibitors of cell death, particularly apoptotic cell death, when administered in cell culture or in vivo. The inhibitors include compounds characterized by general formula I:

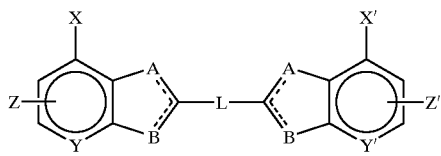

where

- X, X', Z and Z' are independently selected from the group consisting of hydrogen, alkyl, alkoxy, cyano, carboxylic acid or ester, sulfonic acid or ester, amino, alkylamino, nitro, and halogen;

- L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate;

- A====B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen, and where A====B groups on opposing sides of the linker L may be the same or different; and

- Y and Y' are independently selected from carbon and nitrogen.

Preferably, the two groups A====B in a compound are the same. In preferred embodiments, the linker L is selected from $CH_2$, $CHCH_3$, or carbonyl. Additional embodiments include compounds in which A====B represents a three atom linkage effective to form an imidazole ring (e.g. N=C—$NR^1$) or a pyrrole ring (C=N—$NR^1$), that is, benzimidazole or indole compounds, with benzimidazole being preferred. The amine nitrogen of the benzimidazole or indole is preferably substituted with hydrogen or methyl; that is, $NR^1$ is NH or $NCH_3$. The substituents X, X', Z and Z' are preferably independently selected from the group consisting of hydrogen, alkyl, carboxylic acid or ester, amino, nitro, chloro, and fluoro. In further preferred embodiments, at least one of X and X' is amino or nitro, with amino being most preferred. Z and Z' are most preferably selected from the group consisting of hydrogen, carboxylic acid, chloro, and fluoro.

The compositions also include compounds having the general formula II:

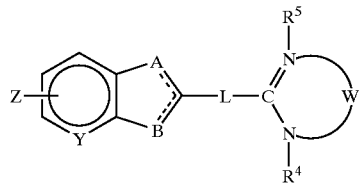

where

- L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate;

- $R^4$ is selected from hydrogen, alkyl, aryl, and aralkyl; and $R^5$ is selected from an electron pair, hydrogen, alkyl, aryl, and aralkyl;

- A====B, as above, represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen;

- Y is carbon or nitrogen;

- W represents a two- to four-carbon alkyl chain linking the two depicted nitrogen atoms to form a five- to seven-membered heterocyclic ring, where each carbon atom of the alkyl chain is unsubstituted or substituted with one or two lower alkyl groups or a hydroxyl group, and is preferably unsubstituted or methyl substituted; and

- Z represents one or more substituents on the aryl ring containing Y, independently selected from the group consisting of hydrogen, alkyl, alkoxy, cyano, carboxylic acid or ester, sulfonic acid or ester, amino, nitro, and halogen.

As above, A====B preferably represents a three atom linkage effective to form an imidazole ring (e.g. N=C—$NR^1$) or a pyrrole ring (C=N—$NR^1$), that is, a benzimidazole or indole compound, with benzimidazole being preferred. The ring on the right side of the linker in formula II is typically an imidazole or imidazoline (or dihydroimidazole), where L is $CR^2R^3$, and $R^5$ represents an electron pair, hydrogen, alkyl, aryl, or aralkyl. Where $R^5$ is not an electron pair, the attached nitrogen atom has a net positive charge (which is formally distributed over the N—C=N moiety in this ring); see, for example, compound SNX 980. Although not depicted as such in formula II, this ring may also be an imidazolyidenyl group; that is, where L is one carbon of an exocyclic double bond, and the ring itself is saturated.

Preferably, the substituents on the linker W are selected from hydrogen and lower alkyl, and most preferably hydrogen and methyl. The heterocyclic ring including W may also be fused to a further carbocyclic ring. The substituent(s) Z are preferably selected from the group consisting of hydrogen; alkyl, carboxylic acid or ester, amino, nitro, chloro, and fluoro; more preferably from hydrogen, lower alkyl, carboxylic acid, chloro, and fluoro; and is most preferably hydrogen.

Also provided are compositions including bis-imidazole or bis-imidazoline compounds of general formula III:

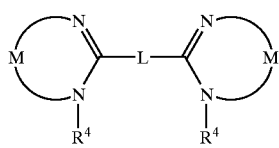

III where

L is $NR^1$, carbonyl, $CR^2R^3$, or a direct bond, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate;

each $R^4$ is independently selected from hydrogen, alkyl, aryl, and aralkyl; and M is —$CR^6R^7$—$CR^8R^9$— or —$CRW$=$CR^8$—, where $R^6$—$R^9$ are independently selected from hydrogen and alkyl.

In preferred embodiments, the linker L is selected from $CH_2$, $CHNH_2$, $CHNO_2$, carbonyl, and a direct bond. The amine nitrogens are preferably substituted with hydrogen or lower alkyl ($R^4$), and the linker M is preferably —$CR^6$=$CR^8$—, such that the rings are imidazole rings, where $R^6$ and $R^8$ are preferably hydrogen or methyl.

A further class of compounds included in the invention is represented by formula IV:

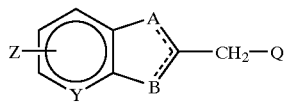

IV where

A===B represents a three-atom linkage effective to form an imidazole, pyrrole, oxazole or thiazole ring fused to the adjacent six-membered ring, where one of A and B is nitrogen or carbon and the other is selected from $NR^1$, O, or S, wherein at least one of A and B is nitrogen;

Y is carbon or nitrogen;

Z represents one or more substituents on the aryl ring containing Y, independently selected from the group consisting of hydrogen, alkyl, alkoxy, cyano, carboxylic acid or ester, sulfonic acid or ester, amino, nitro, and halogen; and Q is selected from cyano, nitro and 2-pyridyl.

In this group of compounds, Y is preferably carbon, and A===B represents a three-atom linkage effective to form an imidazole ring fused to the adjacent six-membered ring; i.e. a benzimidazele; and Z is preferably hydrogen.

It should be understood that the compounds of this invention may exist in other forms depending on solvent, pH, temperature, and other variables known to practitioners skilled in the art. For example, equilibrium forms of many of the compounds may include tautomeric forms.

The compounds may be chemically modified to enhance specific biological properties, such as biological penetration, solubility, oral availability, stability, metabolism, or excretion. The compounds may also be modified to pro-drug forms, such that the active moiety results from the action of metabolic or biochemical processes on the pro-drug.

III. Preparation of Compounds

The compounds of formulas I–IV may be synthesized using a variety of routes known to those in the field. For preparation of compounds of formula I, syntheses may start with substituted benzenes (where R is carbon) or pyridines (where R is nitrogen). Variously substituted benzenes and pyridines are frequently commercially available, or they may be prepared by known methods, typically employing electrophilic aromatic substitution.

Symmetrical bis-benzimidazole compounds of formula I where L is —$CH_2$— may be synthesized, as shown in FIG. 1A, by reacting two equivalents of the correspondingly functionalized ortho-diamino benzene with one equivalent of diethyl malondiimidate. Bis-(4-aza)benzimidazole compounds may be similarly prepared using a 2,3-diamino pyridine. Compounds where A (or B) is O or S (that is, bis-benzoxazoles or bis-benzothiazoles, respectively) may be prepared by substituting an ortho-amino phenol or thiophenol for the ortho-diaminobenzene (or pyridine) referred to above. See, for example, Harnisch, U.S. Pat. No. 3,985,763. Compounds where L is NH or $NR^1$ are prepared by a nucleophilic displacement reaction between a 2-amino- or 2-(alkylamino)-benzimidazole (or benzoxazole or benzothiazole) and a benzimidazole (or benzoxazole or benzothiazole) containing a leaving group at the 2-position, e.g. a 2-bromobenzimidazole.

Unsymmetrically substituted compounds may be synthesized, for example, by reacting one equivalent of a functionalized ortho-diamino benzene (or aminophenol, or aminothiophenol) and one equivalent of a differently functionalized ortho-diamino benzene (or aminophenol or aminothiophenol) with one equivalent of diethyl malondiimidate or substituted malondiimidate, as illustrated by Examples 1–8. Such routes may lead to mixtures, however. An alternate route, illustrated in Example 9 and FIG. 1C for preparation of a bis-benzimidazole, employs a benzimidazol-2-yl imidoate, prepared from the corresponding 2-cyanomethyl benzimidazole (commercially available from Aldrich). This intermediate is reacted with a substituted ortho-diaminobenzene, in this case 3-nitro-1,2-phenylenediamine, to give the bis-benzimidazole (designated herein as SNX 900) as shown. Reduction of the nitro group gave the 4-amino compound, designated herein as SNX 912. A corresponding 2-cyanomethyl benzoxazole, benzothiazole, 4-aza-benzimidazole, or indole may be substituted for the benzimidazole as desired.

Compounds where the bridging carbon is substituted, e.g. with methyl, nitro, amino, or oxo (carbonyl), may be prepared using the corresponding substituted malondiimidate, in protected form if necessary. For example, FIG. 1B illustrates the preparation of a nitro-derivatized bis-benzimidazole compound. Reaction conditions may vary; the compound shown in FIG. 1B was prepared by heating at 180 to 210° C. in trichlorobenzene for two to five hours. A preferred method for forming compounds in which the bridging group is a carbonyl group is illustrated in Examples 14–15. According to this route, a 2-lithiated benzimidazole is reacted with a benzimidazole-2-carboxylate. Either reactant may also be derived from an indole, 2-azabenzimidazole, substituted imidazole, etc.

Compounds of Group II may be prepared by reactions analogous to that shown in FIG. 1C and described above, by substituting the phenylene diamine with the appropriate aliphatic or alicyclic 1,2-diamine. For example, compound 978 (see Table 3, below) may be prepared by reaction of 2-cyanomethyl benzimidazole with 1,2-ethylenediamine. Preparation of other compounds of this group is described in Examples 10–13.

The bis-imidazole or bis-imidazoline compounds of Group III may be prepared by methods analogous to those described for preparation of bis-benzimidazoles, above; i.e. by reaction of a substituted or unsubstituted diethyl malondiimidate with two equivalents of an aliphatic 1,2-diamine. For compounds having a direct bond linker, such as compound 939, below (Table 4), diethyl ethanediimidate is used in place of the malondiimidate. Syntheses of keto-, nitromethylene-, aminomethylene-, and hydroxymethylene-linked bis-imidazoles (e.g. compounds 949–951, below) by a different route have been reported by Joseph et al. (*Synthesis* 7:459, 1977).

Compounds of Group IV may be prepared according to reported methods, again typically based on cyclocondensation reactions of ortho-functionalized anilines. See, for example, Alcalde et al. (*Synthesis* 4:195, 1992), Addison et al. (*J. Heterocyc. Chem.* 20(6):1481, 1983; Loew et al. (U.S. Pat. No. 4,064,136). For example, compound 953, 2-nitromethyl benzimidazole, may be prepared by reaction of 1,2-phenylenediamine with ethyl 2-nitro acetate; compound 914, 2-cyanomethyl benzimidazole, may be prepared by similar reaction with ethyl malonitrile (ethyl 2-cyanoacetate).

IV. Mechanisms of Cell Death
A. Distinction Between Apoptosis and Necrosis Two distinct patterns of pathologic cell death have been described in the literature. The first pattern is consistent with necrosis, a passive process in which collapse of internal homeostasis leads to cellular dissolution (Wyllie et al., 1980a). The process involves loss of integrity of the plasma membrane and subsequent swelling, followed by lysis of the cell (Schwartz et al., 1993). This pattern manifests an early loss of membrane integrity, abnormal organellar morphology, cellular swelling, occurrence in foci, and lysosomal rupture.

The second pattern, consistent with apoptosis, occurs in scattered cells rather than in foci, and features chromatin condensation, nuclear fragmentation, decrease in cellular volume, plasma membrane blebbing, morphological preservation of organellar structure and membrane integrity, budding off of cellular fragments, and retained lysosomal contents (Wyllie et al., 1984). The observation of apoptosis is characterized by condensation of the cytoplasm and nucleus of dying cells. Ultrastructurally, the chromatin becomes electron dense, begins to accumulate at the inner surface of the nuclear envelope, and eventually fills the entire nucleus. The cell breaks up into smaller membrane bound fragments, which may contain individual organelles and remnants of the nucleus, which are rapidly phagocytosed by surrounding cells. As a result, apoptosis is not associated with a classical inflammatory response typical of other forms of cell death, such as necrosis.

Cell death in some tissues can exhibit features characteristic of both apoptosis and necrosis. In these cases, the rate of apoptosis may greatly exceed the rate of phagocytosis, such that the debris of apoptotic cells accumulates and breaks down by a process called secondary necrosis.

B. Neuronal Apoptosis

Apoptosis has been associated with ischemic injury, such as typically occurs in cases of myocardial infarction, reperfusion injury and stroke (Walton et al., 1997; MacManus et al., 1993). Apoptosis is also associated with immunoreactive and immunodegenerative states and a variety of neurodegenerative disorders, including Alzheimer's disease, ALS and motor neuron degeneration, Parkinson's disease, peripheral neuropathy, Down's syndrome, age related macular degeneration (ARMD), Huntington's disease, spinal muscular atrophy, and HIV encephalitis.

Apoptosis has also been implicated as the primary mode of cell death in models of increased intraocular pressure (IOP) in rats and in other experimental procedures that cause retinal ganglion cell loss, including optic nerve transection in monkeys, rabbits, and rats. Recent studies on the mechanism of retinal ganglion cell death in experimental glaucoma indicate that the cells die by apoptosis (Nickells, 1996; Laquis et al., 1998).

Apoptosis can have particularly devastating consequences when it occurs pathologically in cells that do not normally regenerate, such as neurons. Because such cells are not replaced when they die, their loss can lead to debilitating and sometimes fatal dysfunction of the affected organ.

V. In Vitro Model of Apoptosis: Oxygen/Glucose Deprived Retinal Ganglion Cells Assays for apoptotic and/or necrotic death of retinal ganglion cells are useful for selecting compounds that are efficacious in the treatment of disease conditions associated with ischemia, e.g. stroke, glaucoma and other neurodegenerative diseases. An RGC culture system, described in a copending and co-owned U.S. provisional application having U.S. Ser. No. 60/100,241, has been established as a general in vitro model for ischemia, as a model system for specialized forms of ischemia, such as that which manifests in cerebral ischemia and in glaucoma, and for neurodegenerative diseases in general. In the in vitro model for ischemia, cell death is induced by growth factor deprivation and/or oxygen/glucose deprivation (OGD).

A. Obtaining and Culturing Retinal Ganglion Cells

Retinal ganglion cells (RGCs) are central nervous system neurons that extend their axons from the retina through the optic nerve to either the geniculate nucleus or (as in the rat) directly to the superior colliculus or optic tectum. RGCs relay visual signals from the retina to the rest of the brain. These glutamatergic neurons can be purified to almost 100% purity from either the rat or mouse retina using monoclonal antibodies against the surface protein Thy 1 by an immunopanning method, as described in Example 16. RGCs can be kept in culture for a period of four weeks or longer.

B. Methods of Detecting Cell Death in RGC's

Necrotic cell death, as described above, is characterized by loss of cell membrane integrity and permeability to dyes such as propidium iodide (PI), which binds to the DNA of cells undergoing primary and secondary necrosis (Vitale et al., 1993). Necrosis is distinguishable from apoptosis in that cell membranes remain intact in the early stages of apoptosis. A PI dye exclusion assay used in parallel with an assay for apoptosis, as described below, can thus distinguish apoptotic from necrotic cell death.

Detection of programmed cell death, or apoptosis, may be accomplished via staining with annexin V-FITC, a technique known in the art. One of the earliest events in programmed cell death is the translocation of phosphatidylserine, a membrane phospholipid, from the inner side of the plasma membrane to the outer side. Annexin V, a calcium-dependent phospholipid binding protein having a high affinity for membrane bound phosphatidylserine, can thus be used to stain cells undergoing apoptosis, with detection and quantitation of apoptotic cells by flow cytometry or any other method of fluorescent detection (Vermes et al., 1995; Walton et al., 1997).

C. Quantitation of Cell Survival

Necrotic cell death, as described above, is characterized by loss of cell membrane integrity and permeability to dyes such as propidium iodide (PI), which binds to the DNA of cells undergoing primary and secondary necrosis (Vitale et al., 1993). Necrosis is distinguishable from apoptosis in that cell membranes remain intact in the early stages of apoptosis. A PI dye exclusion assay used in parallel with an assay for apoptosis, as described below, can thus distinguish apoptotic from necrotic cell death.

Detection of programmed cell death, or apoptosis, may be accomplished via staining with annexin V-FITC, a technique known in the art. One of the earliest events in programmed cell death is the translocation of phosphatidylserine, a membrane phospholipid, from the inner side of the plasma membrane to the outer side. Annexin V, a calcium-dependent phospholipid binding protein having a high affinity for membrane bound phosphatidylserine, can thus be used to stain cells undergoing apoptosis, with detection and quantitation of apoptotic cells by flow cytometry or any other method of fluorescent detection (Vermes et al., 1995; Walton et al.; 1997).

VI. In Vivo Models of Ischemia

Preferred compositions of the invention are those determined to be efficacious in increasing cell survival in in vitro oxygen/glucose-deprived RGCs, as described in Section V above, by at least 25%, preferably 40%, more preferably 75%, and most preferably 100% or more, relative to untreated control RGCs. Such compositions are further tested in established animal models for ischemia. Various in vivo models have been described that mimic the symptoms of ischemia. These include the gerbil model of global ischemia, produced by transient occlusion of carotid arteries of the gerbil neck (Kirino, 1982), the rat four-vessel occlusion model for global ischemia (Pulsinelli et al., 1979), and the rat middle cerebral artery occlusion (MCAO) model of focal ischemia (Tamura et al., 1981).

Animal stroke models using focal cerebral infarction have been established in cats, dogs, primates, gerbils and rats, and are believed to be directly relevant to clinical experience. The most commonly used focal ischemia model in the rat is the right middle cerebral artery occlusion (MCAO) model developed by Koizumi and co-workers (Koizumi et al., 1986), described in Example 18 below. Briefly, the middle cerebral artery is occluded with nylon filament by insertion from the external carotid artery. The MCAO model requires no craniectomy and allows easy reperfusion. The neuroprotective effect of the subject compounds in this model is described in Section VIIB below.

VII. Biological Activity of Subject Compounds

A. Effect of Compounds on Oxygen/Glucose Deprived RGCs

The extent of protection of RGCs by test compounds was determined as described in Section V above and in Examples 16–17. Each compound was added to control cells and to cells deprived of oxygen and glucose for the time period from 30 minutes prior to OGD, during OGD, and for 24 and 48 hours after OGD. Table 6 gives the value of $EC_{50}$ (concentration at which 50% of cells are protected from cell death relative to control) for series of representative compounds in accordance with structures I–IV.

In Table 5, derivatives of 2,2'-methylenebisbenzimidazole (i.e. formula I where L is —$CH_2$— and Y and Y' are carbon), represented by an asterisk, are named by the substitution on the benzene rings of the benzimidazoles. Structures of additional selected compounds, of structural formulas I through IV, respectively, are shown in Tables 1–4.

TABLE 1

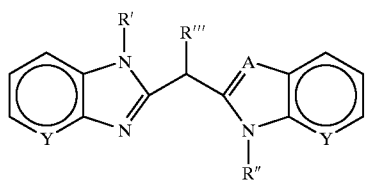

| SNX No. | R' | R" | R'" | Y | A |
|---|---|---|---|---|---|
| 911 | H | H | H | N | N |
| 925 | H | H | $CH_3$ | C | N |
| 952 | $CH_3$ | $CH_3$ | $CH_3$ | C | N |
| 1017 | $CH_3$ | H | =O | C | N |
| 1719 | H | H | =O | C | N |
| 1720 | $CH_3$ | $CH_3$ | =O | C | N |
| 1772 | H | H | =O | C | C |

TABLE 2

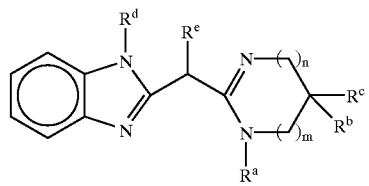

| SNX No. | Ra | Rb | Rc | Rd | Re | n | m |
|---|---|---|---|---|---|---|---|
| 978 | H | H | H | H | H | 1 | 0 |
| 979 | $CH_2Ph$ | H | H | H | H | 1 | 0 |
| 1018 | H | $CH_3$ | H | H | H | 1 | 0 |
| 1019 | $CH_3$ | H | H | H | H | 1 | 0 |
| 1020 | H | $CH_3$ | $CH_3$ | H | H | 1 | 0 |
| 1021 | H | $CH_2CH_3$ | H | H | H | 2 | 0 |
| 1771 | $CH_3$ | H | H | $CH_3$ | $CH_3$ | 1 | 0 |
| 1817 | H | H | OH | H | H | 1 | 1 |
| 1818 | H | H | H | H | H | 2 | 0 |
| 1819 | H | H | H | H | H | 3 | 0 |

TABLE 3

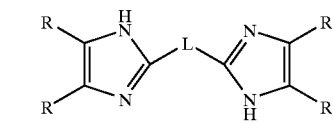

| SNX No. | L | R |
|---|---|---|
| 939 | (bond) | $CH_3$ |
| 949 | $CH(NH_2)$ | H |
| 950 | $CH(NO_2)$ | H |
| 951 | C=O | H |
| 954 | $CH_2$ | H |

TABLE 4

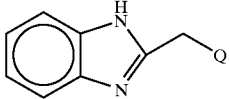

| SNX No. | Q |
|---|---|
| 905 | 2-pyridyl |
| 913 | CH$_3$ |
| 914 | C≡N |
| 953 | NO$_2$ |

TABLE 5

Protection of Oxygen/Glucose Deprived RGCs by Subject Compounds

| Structure No. | SNX No. | EC$_{50}$ (nM) | Name (*indicates substituents on 2,2'-methylenebisbenzimidazole) |
|---|---|---|---|
| I | 952 | 0.4 | 2,2'-ethylidenebis(1-methylbenzimidazole) |
| I | 923 | 0.7 | 4-amino-5'-chloro* |
| I | 1772 | 0.9 | 2-(2'-indolylcarbonyl)benzimidazole |
| I | 1719 | 2.0 | 2,2'-carbonylbisbenzimidazole |
| I | 911 | 2.6 | 2,2'-methylenebis(4-azabenzimidazole) |
| I | 940 | 3.0 | 4-amino-4'-fluoro* |
| I | 903 | 3.2 | 4,4'-diamino* |
| I | 925 | 3.3 | 2,2'-ethylidenebisbenzimidazole |
| I | 977 | 5.0 | 4-amino-5'-carboxylic acid* |
| I | 918 | 6.4 | 4-methyl* |
| I | 917 | 10 | 5,5'-difluoro* |
| I | 1017 | 11 | 1-methyl-2-(2'-indolylcarbonyl)benzimidazole |
| I | 935 | 13 | 4,4'-diamino-5,5'-dichloro* |
| I | 947 | 13 | 4-amino-5-chloro* |
| I | 938 | 22 | 5-nitro* |
| I | 937 | 28 | 4-nitro-5-chloro* |
| I | 944 | 29 | 4-amino-4'-methyl* |
| I | 912 | 31 | 4-amino* |
| I | 936 | 32 | 4-chloro* |
| I | 1720 | 32 | 2,2'-carbonylbis(1-methylbenzimidazole) |
| I | 934 | 84 | 4,4'-dinitro-5,5'-dichloro* |
| I | 924 | 90 | 5,5',6,6'-tetrachloro* |
| I | 904 | 106 | 4,4'-dimethyl* |
| I | 942 | 170 | 4-amino-5'-fluoro* |
| I | 930 | 210 | 4,4'-difluoro* |
| I | 910 | 230 | 1,1'-dimethyl* |
| I | 943 | 260 | 5-amino* |
| I | 1816 | 270 | 2-(4-azabenzimidazol-2-yl)methyl benzimidazole |
| I | 946 | 530 | 4-amino-5'-hydroxyl* |
| I | 909 | 600 | 4,4'-dihydroxyl* |
| I | 897 | 650 | 5,5'-dinitro* |
| I | 898 | 700 | 5,5'-diamino* |
| I | 927 | 2200 | 5,5'-dichloro* |
| I | 901 | 2800 | 4,4'-dinitro* |
| I | 899 | 5300 | 5-chloro* |
| I | 931 | 9300 | 5,5'-dicyano* |
| II | 978 | 0.03 | 2-(4,5-dihydroimidazol-2-yl)methyl benzimidazole |
| II | 1819 | 0.2 | 2-(4,5,6,7-tetrahydro-1,3-diazepin-2-yl)methyl benzimidazole |
| II | 1818 | 0.85 | 2-(3,4,5,6-tetrahydropyrimidin-2-yl)methyl benzimidazole |
| II | 980 | 1.1 | 2-(1,3-dimethyl-4,5-dihydro-1H-imidazol-2-ylmethyl)-1H-benzimidazole |
| II | 979 | 1.4 | 2-(1-benzyl-4,5-dihydroimidazol-2-yl)methyl benzimidazole |
| II | 1817 | 2.0 | 2-(3,4,5,6-tetrahydro-5-hydroxypyrimidin-2-yl)methyl benzimidazole |
| II | 1771 | 2.0 | 1-methyl-2-[(1-methyl-4,5-dihydroimidazol-2-yl)ethyl benzimidazole |
| II | 1019 | 10 | 2-(1-methyl-4,5-dihydroimidazol-2-yl)methyl benzimidazole |
| II | 1020 | 10 | 2-(4,4'-dimethyl-5-hydroxyimidazol-2-yl)methyl benzimidazole |
| II | 1018 | 100 | 2-(4-methyl-4,5-dihydroimidazol-2-yl)methyl benzimidazole |
| II | 1021 | 100 | 2-(4-ethyl-3,4,5,6-tetrahydropyrimidin-2-yl)methyl benzimidazole |
| III | 949 | 0.19 | 2,2'-(aminomethylene)bisimidazole |
| III | 951 | 0.21 | di(imidazol-2-yl)methanone |
| III | 939 | 3.8 | 2,2'-bis(4,5-dimethylimidazole) |
| IV | 953 | 0.4 | 2-(nitromethyl)benzimidazole |
| IV | 914 | 18 | 2-(cyanomethyl)benzimidazole |

TABLE 5-continued

Protection of Oxygen/Glucose Deprived RGCs by Subject Compounds

| Structure No. | SNX No. | $EC_{50}$ (nM) | Name (*indicates substituents on 2,2'-methylenebisbenzimidazole) |
|---|---|---|---|
| IV | 913 | 62 | 2-methylbenzimidazole |
| IV | 905 | 80 | 2-(2-pyridylmethyl)benzimidazole |

As can be seen from the data in Table 5, below, the compounds protected neurons from apoptotic cell death, compared to untreated control OGD cells, some at very low concentrations.

Table 6, below, shows dose-dependent data (increase in survival compared to OGD control, in a similar assay) for selected bis-benzimidazole compounds of formula I. Symbols in the Table are interpreted as follows:

B. Effect of Subject Compounds on Infarct Volume in in vivo Stroke Model

Compounds were administered by either an IV (intravenous) or ICV (intracerebroventricular) route in the MCAO model, described above and in Example 18. The

TABLE 6

Increase in Survival of OGD Cells Treated with Subject Compounds

| Cmpd No. Substitution Concn, µM | SNX857 none | SNX899 5-Cl | SNX900 4-$NO_2$ | SNX901 4,4'-$NO_2$ | SNX903 4,4'-$NH_2$ | SNX904 4,4'-Me | SNX909 4,4'-OH | SNX910 N,N'-Me |
|---|---|---|---|---|---|---|---|---|
| | | | Percent Increase in Survival over OGD Control Cells | | | | | |
| 0.01 | + | + | ++ | ++ | +++ | + | + | ++ |
| 0.1 | +++ | ++ | +++ | ++ | +++ | +++ | ++ | ++ |
| .1 | ++ | ++ | ++ | +++ | +++ | +++ | +++ | +++ |
| 10 | +++ | + | + | +++ | ++ | — | + | + |

| Cmpd. No. Substitution Concn, µM | SNX912 4-$NH_2$ | SNX923 4-$NH_2$-5'-Cl | SNX925 ethylidene | SNX929 4,4'-$CF_3$ | SNX930 4,4'-F | SNX931 5,5'-CN | SNX897 5,5'-$NO_2$ | SNX898 5,5'-$NH_2$ | SNX899 5-Cl |
|---|---|---|---|---|---|---|---|---|---|
| | | | Percent Increase in Survival over OGD Control Cells | | | | | | |
| 0.001 | ++ | +++ | ++ | + | + | — | nd | nd | nd |
| 0.01 | ++ | +++ | +++ | ++ | +++ | + | ++ | + | + |
| 0.1 | ++ | +++ | +++ | ++ | + | + | ++ | + | ++ |
| 1 | +++ | +++ | +++ | + | ++ | — | ++ | + | ++ |
| 10 | +++ | +++ | +++ | — | ++ | ++ | nd | — | + |

+up to 50% increase
++50%–100% increase
+++>100% increase
—negligible or no increase
nd not determined As shown in Tables 5 and 6, bis-benzimidazole compounds (Structure I) having substituents at one or both 4 positions, e.g. amino, nitro, methyl, trifluoromethyl, fluoro, or hydroxyl (SNX 900, 901, 903, 904, 909, 912, 923, 929, and 930) were more effective overall than the unsubstituted compound, although for the methyl- and trifluoromethyl-substituted compounds, there were signs of toxic effects at higher doses (i.e. 10 µM). Compounds with 4-amino substitution were particularly effective. Compounds with methyl substitution on the ring nitrogens (SNX 904) or at the bridging carbon (SNX 925) as well as compounds having pyridine rings (SNX 911) were also very effective. Bis-benzimidazole compounds having only 5 or 5,5' substitution (e.g. the last four entries in Table 6) were generally less effective than the 4-substituted counterparts. Compounds of Structures II–IV, i.e. various substituted bis-imidazoles (e.g. SNX 949, 951, 939) and benzimidazole-dihydroimidazole, -tetrahydropyrimidine, and -tetrahydro-1,3-diazepine compounds (e.g. SNX 978, 979, 980, 1019, 1020, 1771, 1818, and 1819) were also very effective, some giving $EC_{50}$'s in the sub-nanomolar range (Table 5).

extent of ischemic damage in the absence and presence of compound was assessed by visualization of coronal brain slices. Conversion of 2,3,5-triphenyltetrazolium chloride (TTC) to formazan in normal tissue produces a red color. Unstained areas (white) constitute the infarct, whereas pink areas between white (infarction) and red stained areas (normal brain) define the ischemia penumbra. Preliminary studies confirmed that tissues stained pink contained mixed populations of living and dead cells.

Figure 3:
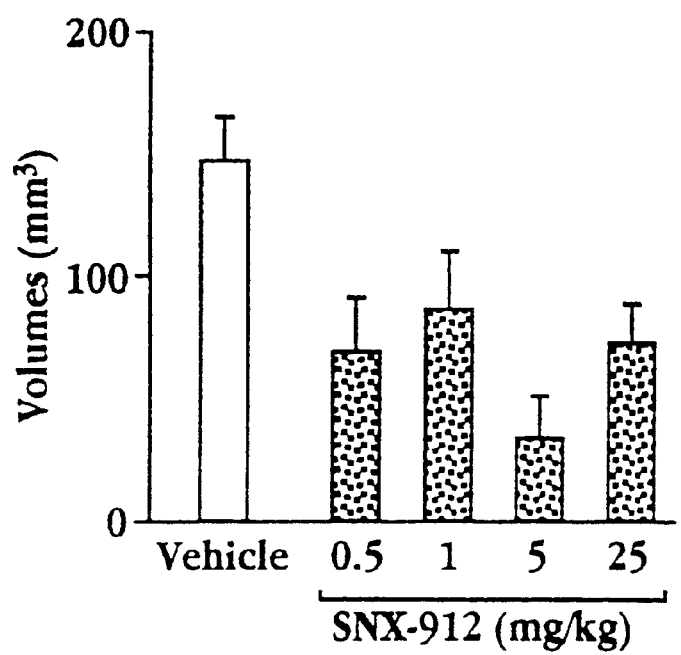
FIG. 3 shows dose-response data for SNX 912 in the study illustrated in FIG. 2.
Figure 4:
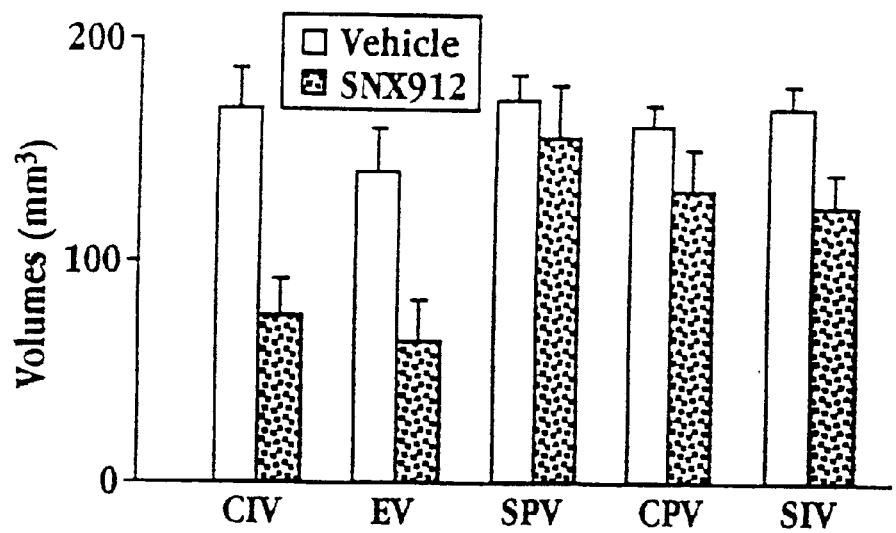
FIG. 4 shows the effect of IV (intravenous) administration of SNX 912 on ischemic volume and infarct volume in the MCAO in vivo stroke model.
Figure 5:
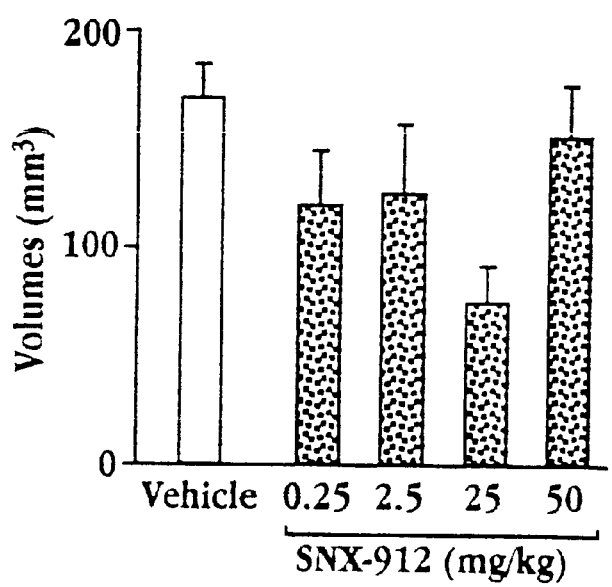
FIG. 5 shows dose-response data for SNX 912 in the study illustrated in FIG. 4.

Table 3 shows the decrease in infarct and edema volumes (i.e., % protection) in subjects which received test compound SNX 912 (4-amino compound) in the dosages shown, ICV pre-MCAO, or IV immediately following reperfusion, after two hours MCAO, as compared to control subjects which received deionized water. Results are also illustrated in FIGS. 2–3 for ICV administration and FIGS. 4–5 for IV administration.

As the data show, significant protection was afforded with respect to ischemic volume and infarct volume. ICV administration, a more efficient route of delivery, generally gave greater protection at a smaller dose.

TABLE 7

Effect of SNX 912 (2,2'-methylenebis(4-amino)benzimidazole) in Reducing Ischemic Damage in the Brain

| Affected Area | IV (25 mg/kg) % Protection | IV (25 mg/kg) Probability | ICV (5 mg/kg) % Protection | ICV (5 mg/kg) Probability |
| --- | --- | --- | --- | --- |
| Total ischemic volume | 32% | $p < 0.05$ | 47% | $p < 0.01$ |
| Total infarct volume | 55% | $p < 0.05$ | 76% | $p < 0.01$ |
| Cortical infarct volume | 53% | $p < 0.05$ | 76% | $p < 0.01$ |
| Subcortical infarct volume | 55% | $p > 0.05$ | 75% | $p < 0.05$ |
| Cortical penumbra | 10% | $p > 0.05$ | 30% | $p < 0.05$ |
| Subcortical penumbra | 18% | $p > 0.05$ | 7% | $p < 0.05$ |
| Edema | 26% | $p > 0.01$ | 80% | $p < 0.01$ |

C. Effect of Compounds on Oxygen/Glucose Deprived Cardiac Myocytes

The hypoxic cardiac myocyte (CM) has been used as a simplified model of myocardial ischemia. In the present study, cultures of CM's were deprived of oxygen and glucose for 8 hours, then also exposed to 24–48 hours reoxygenation. It is known that reperfusion of the damaged areas can be one of the major mechanisms of myocardial cellular injury. The OGD cells, as well as non-OGD control cells, were treated with SNX 912 for the time period from 30 minutes prior to OGD, during OGD, and for 24 and 48 hours after OGD. Cell survival was quantitated as described above.

Administration of SNX 912 protected the cardiac myocytes from apoptotic cell death, compared to untreated OGD cells, in a dose dependent manner. $EC_{50}$ and TI (therapeutic index) for SNX 912 in the tests were as follows: For 8 hrs OGD/24 hrs reoxygenation, $EC_{50}$=310 nM and TI>30; for 8 hours OGD and 48 hrs reoxygenation, $EC_{50}$=55 nM and TI>200.

TABLE 8

Effect of SNX 912 (4-amino bisbenzimidazolylmethane) in Reducing Ischemic Damage in Cardiac Cells

| Hours OGD | Hours reoxygenation | $EC_{50}$ | TI |
| --- | --- | --- | --- |
| 8 | 24 | 310 nM | >30 |
| 8 | 48 | 55 nM | >200 |

VII. Methods of Treatment

In accordance with the invention, cell death is inhibited by administering, in a pharmaceutically acceptable carrier, a compound represented by any of formulas I through IV, discussed above, or pharmaceutically acceptable salts. Preferred compounds are also discussed above, and particularly include those giving $EC_{50}$ values, for the assay represented in Table 1, of about 500 nm or less, preferably about 100 nm or less, and more preferably about 50 nm or less.

The compositions may be used for the treatment of diseases that involve apoptotic cell death or other forms of interventional cell death. The method of treatment, dosage level, paradigm of administration, etc., may be selected from conventional methods and techniques. For example, a compound of this invention may be administered with a pharmaceutically acceptable adjuvant to a patient suffering from a disease or disorder resulting from sudden and/or pathological cell death. The compound is administered, in combination with an acceptable adjuvant or carrier, in an amount effective to lessen the severity of the disease as a result of decreasing the biological cell death.

The compounds of formulas I–IV may be used alone or in combination, and they may be combined with other classes of cell death-inhibiting compounds, to increase the effect of therapy, or as a prophylaxis to decrease the progression of a cell death-induced disease. The compounds of this invention may also be used in combination with other therapeutic agents, including anti-hypertensive agents, antibiotics, immunomodulators or anti-inflammatory agents. In combination therapy, the compounds may be administered either sequentially or concurrently.

Pharmaceutical compositions of this invention comprise any of the compounds of formulas I–IV and their pharmaceutically acceptable salts, together with pharmaceutically acceptable carriers, adjuvants or vehicles. The pharmaceutical compositions may be administered orally, parenterally (which includes subcutaneous, intravenous, intramuscular, intra-articular, intracutaneous, intrasynovial, intrastemal, intrathecal, epidural, intralesional, intracerebroventricular, or intracranial), by inhalation spray, topically, rectally, nasally, buccally, vaginally, or via an implanted reservoir. Injectable preparations include a sterile injectable aqueous or oil composition or a suspension. For treatment or prevention of damage resulting from therapeutic intervention in cardiac cells, e.g. during arterial graft or angioplasty, the compounds may be administered locally, e.g. by catheter or stent, to the affected artery.

As shown above, dosages of 5 mg/kg SNX 912 were effective in reducing post-ischemic damage in rats via ICV administration, and a higher dose (25 mg/kg) was effective via IV administration, a more convenient but less efficient route. Nanomolar concentrations of the compound were effective in protection of cardiac cells in vitro. Appropriate dosages of other compounds of the invention may be higher or lower, depending on the potency of the particular compound. Relative potencies of a variety of compounds are given above, and others may be determined in assays as described herein. As always, optimum dosages in human therapy will vary according to factors such as the route of administration, the age of the patient, other existing medical conditions, and the type and severity of symptoms, and may be determined according to standard methods known to skilled practitioners.

VIII. Indications

Cell death-mediated conditions which may be treated or prevented by the compositions of the invention include ischemic injury, such as stroke or myocardial infarction, ischemic diseases, inflammatory diseases, trauma, including myocardial damage, autoimmune diseases, and neurodegenerative diseases.

Ischemic damage to the central nervous system (CNS) may result from either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors. Ischemic diseases include cerebral ischemia, such as results from stroke, myocardial infarction, retinal ischemia, macular degeneration, and glaucoma.

Various neurodegenerative diseases which may involve apoptotic cell death include Alzheimer's disease (Kim et al., 1997), ALS and motor neuron degeneration (Greenlund et al., 1995), Parkinson's disease (Ghosh et al., 1994), peripheral neuropathies (Batistatou et al., 1993), Down's syndrome (Busciglio et al., 1995), age related macular degeneration (ARMD) (Hinton et al., 1998), Huntington's disease (Goldberg et al., 1996), spinal muscular atrophy (Liston et al., 1996), and HIV encephalitis (Lazdins et al., 1997).

Although the invention has been described with respect to particular treatment methods and composition, it will be apparent to those skilled that various changes and modifications can be made without departing from the invention.

EXAMPLES

The following examples illustrate but are not intended in any way to limit the invention.

Example 1

Preparation of 2-[(5-Chloro-1H-benzimidazol-2-yl)methyl]-4-nitro-1H-benzimidazole To a flame-dried 100 mL round-bottom flask equipped with a stir bar and a reflux condenser were added 4-chloro-1,2-phenylenediamine (1 g; 7.0 mmoles), 3-nitro-1,2-phenylenediamine (1.07 g; 7.0 mmoles), diethyl malonimidate dihydrochloride (1.62 g; 7.0 mmoles) and ultra pure acetic acid (ca. 35 mL; from Aldrich) under a nitrogen atmosphere. The mixture was refluxed for 2 hours and then cooled to room temperature, and the acetic acid was removed (via roto-vap). The residue was suspended and sonicated (ca. 5 minutes) in 0.5 M HCl, and the remaining precipitate was removed by filtration and dried ($P_2O_5$ and high-vacuum). This procedure gave 0.8 g of the desired 2-[(5-chloro-1H-benzimidazol-2-yl)methyl]4-nitro-1H-benzimidazole as a dark brown solid in 35% yield. It gave one major peak by HPLC and had mass spec (FB+): m/z= 328.0 [M+].

Example 2

Preparation of 2-[(5-Chloro-1H-benzimidazol-2-yl)methyl]-1H-benzimidazol-4-amine (SNX 923)

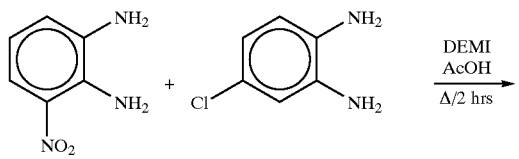

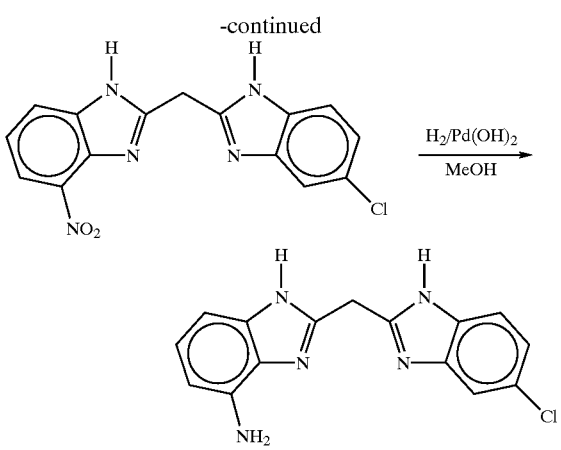

General Procedure 1 (Cyclocondensation):

To a 100 mL round bottom flask (RBF) equipped with a reflux condenser and a stir bar under a blanket of nitrogen were added 3-nitro-1,2-phenylenediamine (0.50 g; 3.26 mmoles), 4-chloro-1,2-phenylenediamine (0.46 g; 3.26 mmoles), diethyl malonimidate dihydrochloride (1.1 eq.; 0.83 g; 3.60 mmoles) and acetic acid (25 mL). The reaction was maintained at reflux for two hours and then cooled to room temperature. The solvent was removed on a rotovapor, and the remaining solid was suspended in dilute HCl (ca. 75 mL). The pH was brought to $^{18}6$ using 5M NaOH, and the precipitate was collected and air-dried at room temperature for several hours.

General Procedure 2 (Reduction):

The crude mixture of three compounds was added to a 250 mL RBF and dissolved in methanol (ca. 35 mL). Degussa's catalyst (50 mg) was added, the flask was sealed with a rubber septum, and hydrogen gas was flushed through the flask for 10 minutes. The reaction mixture was maintained under a hydrogen atmosphere overnight (via a balloon) and then filtered with the aid of Celite®. The methanol was removed and the crude solid was taken up in 10 mL of dilute HCl, purified by preparative HPLC (5% acetonitrile with 0.1% TFA for 5 minutes then 5% to 95% over 45 minutes) and converted to the HCl salt by three freeze drying cycles with dilute HCl. his procedure gave 0.110 g of pure 2-[(5-chloro-1H-benzimidazol-2-yl)methyl]-1H-benzimidazol-4-amine dihydrochloride in 10% yield. It had MS: m/z=297.1 [$M^{+1}$] amu and gave one peak on HPLC at both 210 and 280 nm (14.32 minutes using the JWTFACN gradient).

Example 3

Preparation of 5-Chloro-2-[(5-chloro-4-nitro-1H-benzimidazol-2-yl)methyl]-4-nitro-1H-benzimidazole (SNX 934)

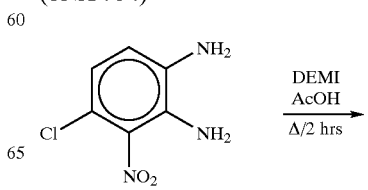

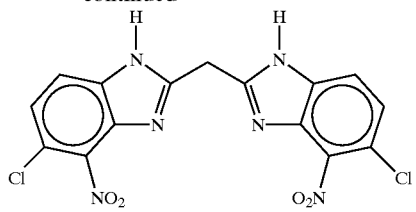

The following components were reacted according to General Procedure 1, above: 4-chloro-3-nitro-1,2-benzenediamine (1.0 g; 5.33 mmoles), diethyl malonimidate dihydrochloride (1.1 eq.; 0.95 g; 2.93 mmoles) and acetic acid (35 mL). The resulting solid was dissolved in dilute HCl (with heat) and freeze-dried to give 1.56 grams of 5-chloro-2-[(5-chloro-4-nitro-1H-benzimidazol-2-yl)methyl]4-nitro-1H-benzimidazole in 61% yield. It had MS: m/z=406.0 [M$^{+1}$] amu and gave one peak on HPLC at both 210 and 280 nm (26.99 minutes using the JWTFACN gradient).

Example 4

Preparation of 2-[(4-Amino-5-chloro-1H-benzimidazol-2-yl)methyl]-5-chloro-1H-benzimidazol4-amine (SNX 935)

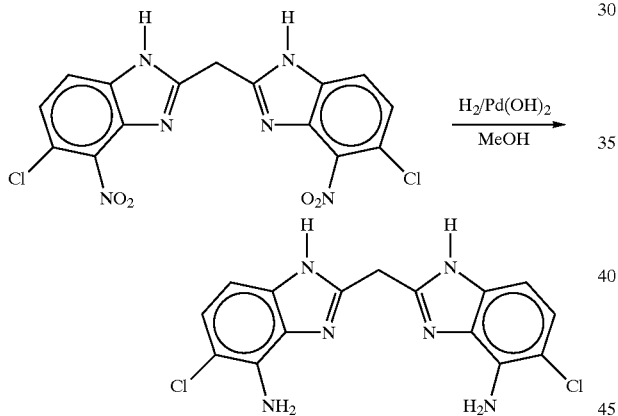

SNX 934 (5-chloro-2-[(5-chloro-4-nitro-1H-benzimidazol-2-yl)methyl]4-nitro-1H-benzimidazole; 125 mg; 3.1 mmoles) was reduced according to General Procedure 2, above. The crude solid product was taken up in 10 mL of dilute HCl, purified by preparative HPLC (25% acetonitrile/0.1% TFA to 75% acetonitrile over 50 minutes) and converted to the HCl salt by three freeze drying cycles with dilute HCl. This procedure gave 89 mg of 2-[(4-amino-5-chloro-1H-benzimidazol-2-yl)methyl]-5-chloro-1H-benzimidazol-4-amine dihydrochloride in 68% yield. It had MS: m/z=346.1 [M$^{+1}$] amu and gave one peak on HPLC at both 210 and 280 nm (17.88 minutes using the JWTFACN gradient).

Example 5

Prearation of 2-[(4-Fluoro-1H-benzimidazol-2-yl)methyl]-1H-benzimidazol-4-ylamine (SNX 940)

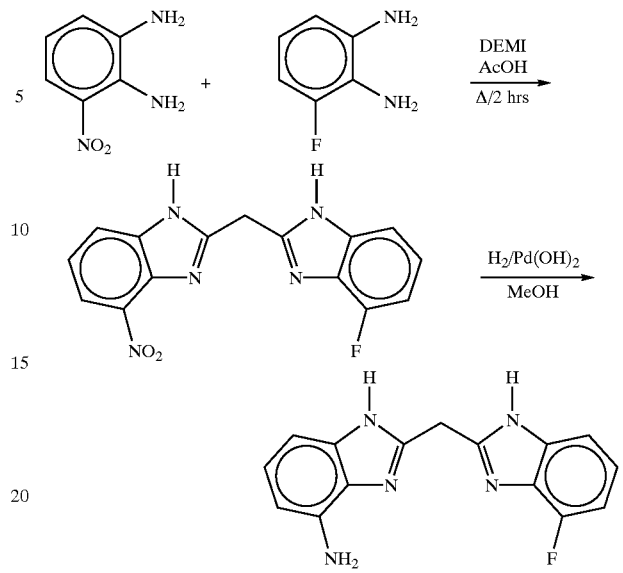

The following components were reacted according to General Procedure 1, above: 3-nitro-1,2-phenylenediamine (0.50 g; 3.26 mmoles), 3-fluoro-1,2-phenylenediamine (0.41 g; 3.26 mmoles), diethyl malonimidate dihydrochloride (1.1 eq.; 0.83 g; 3.60 mmoles) and acetic acid (25 mL). The crude mixture of three compounds was then reduced according to General Procedure 2, above. The crude solid product was taken up in 10 mL of dilute HCl, purified by preparative HPLC (25 to 75% acetonitrile (with 0.1% TFA) over 50 minutes) and converted to the HCl salt by three freeze drying cycles with dilute HCl. This procedure gave 0.208 g of pure 2-[(4-fluoro-1H-benzimidazol-2-yl)methyl]-1H-benzimidazol-4-ylamine dihydrochloride in 18% yield. It had MS: m/z=282.2 [M$^{+1}$] amu and gave one peak on HPLC at both 210 and 280 nm (12.99 minutes using the JWTFACN gradient).

Example 6

Preparation of 2-[(4-Methyl-1H-benzimidazol-2-yl)methyl]-1H-benzimidazol-4-ylamine (SNX 944)

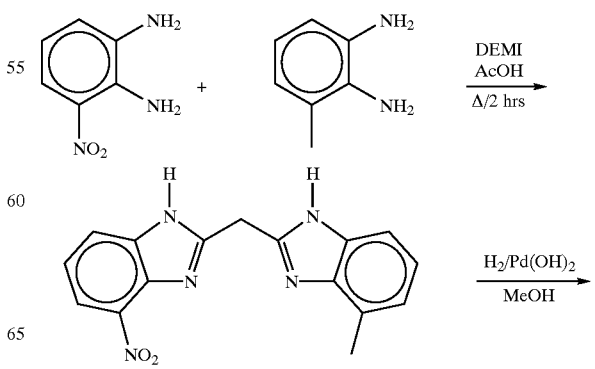

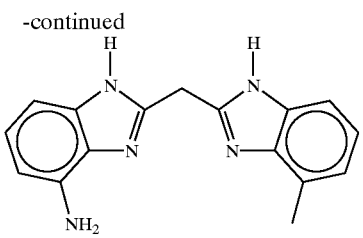

The following components were reacted according to General Procedure 1, above: 3-nitro-1,2-phenylenediamine (0.5 g; 3.26 mmoles), 3-methyl-1,2-phenylenediamine (0.4 g; 3.26 mmoles), diethyl malonimidate dihydrochloride (1.1 eq.; 0.83 g; 3.60 mmoles) and acetic acid (25 mL). The crude mixture of three compounds was then reduced according to General Procedure 2, above. The crude solid product was taken up in 10 mL of dilute HCl, purified by preparative HPLC (15 to 75% acetonitrile (with 0.1% TFA) over 60 minutes) and converted to the HCl salt by three freeze drying cycles with dilute HCl. This procedure gave 0.42 g of pure 2-[(4-methyl-1H-benzimidazol-2-yl)methyl]-1H-benzimidazol-4-ylamine dihydrochloride in 37% yield. It had MS: m/z=278.2 [$M^{+1}$] amu and gave one peak on HPLC at both 210 and 280 nm (12.01 minutes using the JWTFACN gradient).

Example 7

Preparation of 2-[(4-Amino-1H-benzimidazol-2-yl)methyl]-1H-benzimidazole-5 carboxylic Acid (SNX 977)

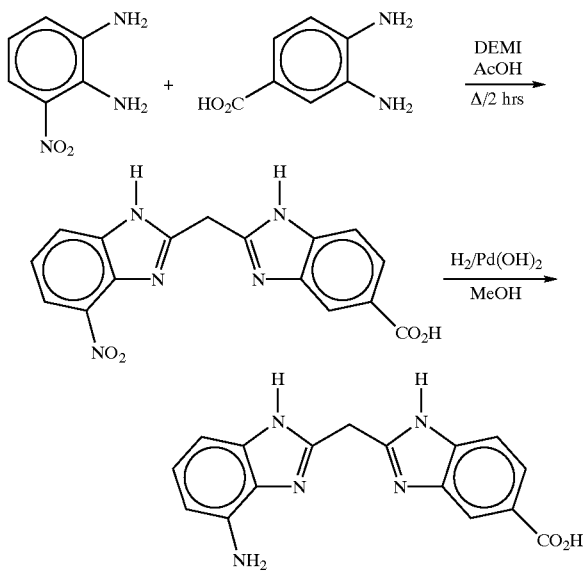

The following components were reacted according to General Procedure 1, above: 3-nitro-1,2-phenylenediamine (0.50 g; 3.26 mmoles) 3,4-diaminobenzoic acid (0.40 g; 3.26 mmoles), diethyl malonimidate dihydrochloride (1.1 eq.; 0.83 g; 3.60 mmoles) and acetic acid (25 mL). The crude mixture of three compounds was then reduced according to General Procedure 2, above. The crude solid product was taken up in 10 mL of dilute HCl, purified by preparative HPLC (2 to 40% acetonitrile (with 0.1% TFA) over 60 minutes) and converted to the HCl salt by three freeze drying cycles with dilute HCl. This procedure gave 0.213 g of pure 2-[(4-amino-1H-benzimidazol-2-yl)methyl]-1H-benzimidazole-5-carboxylic acid dihydrochloride in 17% yield. It had MS: m/z=308.2 [$M^{+1}$] amu and gave one peak on HPLC at both 210 and 280 nm (10.20 minutes using the JWTFACN gradient).

Example 8

Preparation of 2-[(4-Amino-1H-benzimidazol-2-yl)methyl]-1H-benzimidazole-4-carboxylic acid (SNX 1799)

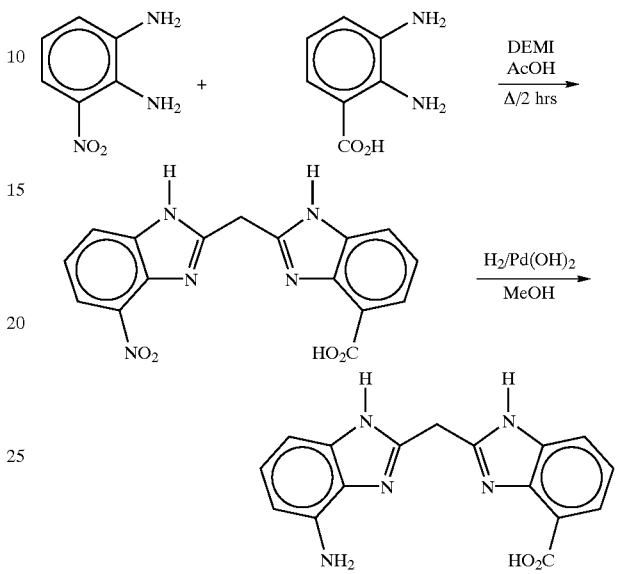

The following components were reacted according to General Procedure 1, above: 3-nitro-1,2-phenylenediamine (0.50 g; 3.26 mmoles) 2,3-diaminobenzoic acid (0.40 g; 3.26 mmoles), diethyl malonimidate dihydrochloride (1.1 eq.; 0.83 g; 3.60 mmoles) and acetic acid (25 mL). The crude mixture of three compounds was then reduced according to General Procedure 2, above. The crude solid was taken up in 10 mL of dilute HCl, purified by preparative HPLC (2 to 40% acetonitrile (with 0.1% TFA) over 60 minutes) and converted to the HCl salt by three freeze drying cycles with dilute HCl. This procedure gave 0.103 g of pure 2-[(4-amino-1H-benzimidazol-2-yl)methyl]-1H-benzimidazole-4-carboxylic acid dihydrochloride in 8% yield. It had MS: m/z=308.2 [$M^{+1}$] amu and gave one peak on HPLC at both 210 and 280 nm (10.20 minutes using the JWTFACN gradient).

Example 9

Preparation of 2,2'-Methylenebis(4-nitro)benzimidazole (SNX 900) and 2,2'-methylenebis(4-amino)benzimidazole (SNX 912)

A flame-dried 3 L 3-neck round-bottom flask was equipped with a stir bar, thermometer and 2-benzimidazolylacetonitrile (35.9 g; 228 mmoles) and then stoppered. The flask was opened to an oil bubbler to allow for a gentle stream of dry nitrogen. Anhydrous toluene (750 mL) was then added by cannula, followed by the addition of anhydrous denatured ethanol (33 mL; 2.4 equiv.) by syringe. The suspension was chilled at a temperature of 0° C., the nitrogen stream was stopped, and HCl gas was bubbled in. HCl was added at such a rate that the temperature of the solution did not exceed 15° C., until saturated, whereupon the ice bath was removed. The reaction was allowed to stir at room temperature overnight. Anhydrous diethyl ether (3 L) was added, and the mixture was chilled on an ice bath. The solid was collected by filtration under nitrogen into a Schlenk tube and dried under high vacuum. The product, ethyl 2-(1H-benzimidazol-2-yl) ethanimidoate (see FIG. 1C), was used in the next step without further analysis or purification.

Using Airless-Ware®, the ethyl 2-(1H-benzimidazol-2-yl) ethanimidoate was transferred, under a nitrogen atmosphere, to a flame-dried 2-neck 3 L round-bottom flask equipped with a stir bar and a refluxing condenser, with a drying tube at one neck and a rubber septum at the other neck. Anhydrous ethanol (ca. 500 mL) was added via cannula with stirring. To a separate flame-dried 1 L round-bottom flask were added 3-nitro-1,2-phenylenediamine (35 g; 228 mmoles) and anhydrous ethanol (ca. 500 mL) under a nitrogen atmosphere. The flask was heated until the nitro compound dissolved and the contents, while still hot, were added quickly to the stirred solution of ethyl 2-(1H-benzimidazol-2-yl)ethanimidoate via cannula. The contents were quickly brought to reflux and refluxed overnight with stirring. The solvent was removed (roto-vap) and the solid residue was suspended in 1N HCl (ca. 1 L) and heated until dissolved. The hot solution was filtered and allowed to cool to room temperature whereupon 2-(1H-benzimidazol-2-ylmethyl)4-nitro-1H-benzimidazole was crystallized as the dihydrochloride salt. The solid was removed by filtration and dried under high-vacuum. This procedure gave 57 grams (69%) of pure 2-(1H-benzimidazol-2-ylmethyl)4-nitro-1H-benzimidazole dihydrochloride as a gray solid. It gave one peak by HPLC and had mass spec (FB+): m/z=294 [M+].

Reduction of the nitro group gave the 4-amino compound, designated herein as SNX 912. MS: [M+1] 264.

Example 10
Preparation of 2-(6-Ethyl-1,4,5,6-tetrahydro-pyrimidine-2-ylmethyl)-1H-benzimidazole dihydrochloride (SNX 1021)

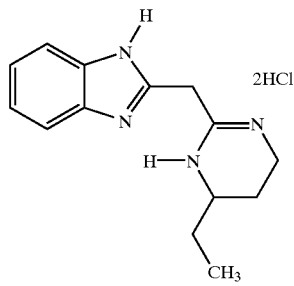

General Procedure 3 (Cyclocondensation):

The intermediate ethyl 2-(1H-benzimidazol-2-yl) ethanimidoate (5–10 mmol), prepared as described in Example 9, was transferred from a storage Schlenk tube to a pre-tared, oven-dried two necked round bottom flask equipped with a stir bar, under a gentle stream of argon, without exposing the solid to air. The two necked flask and contents were removed from the empty Schlenk tube and stoppered under argon, and the weight of the solid was obtained by difference. One stopper was then replaced with an oven-dried water jacketed condenser fitted with a drying tube containing Drierite. Ethyl alcohol (anhydrous) was cannulated into the flask under argon pressure, and the resulting suspension was stirred and placed over a heating mantle. Before the contents reached reflux, 1.1 eq. of 1,3-diamino-pentane was added slowly to the suspension via syringe. The heat was adjusted to the lowest possible setting for reflux to continue. After 12 hours, the resulting solution was concentrated by rotary evaporation, and the residue was dissolved in water, filtered and preparatively fractionated by reverse-phase HPLC. The fractions containing the desired product (with the expected molecular weight) were pooled and concentrated to dryness. The resulting solid was dissolved 15 mL of 0.5M HCl and concentrated; this procedure was repeated twice. The white solid obtained gave the following analytical data: $^1$H NMR: 0.938 ppm (t, 3H); 1.526 (quintet, 1H), 1.694 (quintet, 2H); 2.046 (quintet, 1H); 3.421 (t, 2H); 3.518 (quintet, 1H); 4.594 ppm (d, 2H); 7.488 ppm (q, 2H); 7.785 ppm (q, 2H). Mass Spectrum: [M+1]$^+$= 243.2.

Example 11
Preparation of 2-(5,5-Dimethyl-4,5-dihydro-1H-imidazol-2-ylmethyl)-1H-benzimidazole dihydrochloride (SNX 1020)

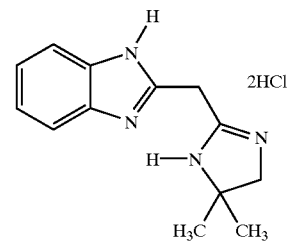

General Procedure 3 was repeated, using 1,2-diamino-2-methyl propane in place of 1,3-diamino-pentane. The white solid obtained gave the following analytical data: $^1$H NMR: 1.388 ppm (s, 6H); 3.657 ppm (s, 2H); 4.620 ppm (s,2H); 7.484 ppm (q, 2H); 7.784 (q, 2H). Mass spectrum: [M+1]$^+$= 229.1.

Example 12
Preparation of (4-Nitro-5-chloro-benzimidazol-2yl-benzimidazole) Methane Dihydrochloride (SNX 937)

General Procedure 3 was repeated, using 1,2-diamino-2-methyl propane in place of 1,3-diamino-pentane. The crude product, a dark brown solid, was dissolved 15 mL of 0.5M HCl and concentrated; this procedure was repeated twice. The solid obtained gave the following analytical data: $^1$H NMR: 5.029 ppm (s, 2H); 7.465 ppm (d, 1H); 7.50 ppm (dd, 2H); 7.75 ppm (dd, 2H); 7.885 ppm (d, 1H). mass spectrum: [M+1]$^+$=329.

Example 13
Preparation of 2-(1,3-Dimethyl-4,5-dihydro-1H-imidazol-2-ylmethyl)-1H-benzimidazole Hydrogen Dichloride: (SNX 980)

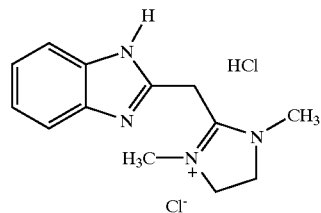

General Procedure 3 was repeated, using N,N'-dimethylethylenediamine in place of 1,3-diamino-pentane. The resulting white solid gave the following analytical data: $^1$H NMR: 7.670 ppm (q, 2H); 7.340 ppm (q, 2H); 4.654 ppm (s, 2H); 4.6 ppm (very broad s, 1H); 3.917 ppm (s, 4H); 3.119 ppm (s, 6H). Mass Spectrum: [M+1]$^+$=229.1.

Example 14
Preparation of (1H-Indol-2-yl)-(1-methyl-1H-benzimidazol-2-yl)-methanone Hydrochloride (SNX 1017)

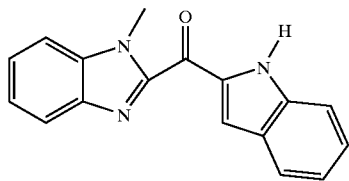

A solution of N-methyl-benzimidazole (1.32 g, 10.0 mmol) in 50 ml anhydrous tetrahydrofuran was cooled to −78° C. under a nitrogen atmosphere. n-Butyl lithium (4.08 ml, 10.2 mmol; 2.5 M in hexane) was slowly added at −78° C. After 30 min stirring, the solution was quenched with a solution of ethyl indole-2-carboxylate (1.98 g, 10.5 mmol) in 50 ml tetrahydrofuran 50 ml at −78° C. The solution was then allowed to warm to room temperature. After 6 h, the solution was quenched with aq. ammonium chloride (20 ml) diluted with diethyl ether (150 ml) The organic layer was dried over anhydrous sodium sulfate, filtered, and concentrated to give the crude product, which was purified by HPLC. Yield 150 mg, (40%). MS: [M+1] 276.

Example 15
Preparation of bis-(1H-Benzimidazol-2-yl)methanone Dihydrochloride (SNX 1719)

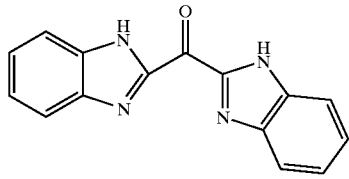

To a suspension of benzimidazole (1.18 g, 10.0 mmol) in tetrahydrofuran was added formaldehyde 1 ml (1.0 eq. 37% water solution) at room temperature (for protection of the ring amino groups). After 10 minites, the solvent was removed on a rotavapor, and the intermediate (1-hydroxymethyl) benzimidazole was dried in vacuo for 24 h.

A solution of (1-hydroxymethyl)benzimidazole in anhydrous THF (50 ml) was cooled to −78° C. under nitrogen atmosphere, and tert-butyl lithium (6.8 ml, 10.2 mmol; 1.5 M in pentane) was slowly added at −78° C. The solution was allowed to warm at −20° C. and maintained for 1 h with stirring to give a homogeneous yellow to orange solution. The solution was treated with a solution of carbonyldiimidazole (0.08 g, 0.5 mmol) in 50 ml THF at −78° C., then allowed to warm to room temperature. After 6 h, the solution was quenched with aqueous $NH_4Cl$ (20 ml) diluted with diethyl ether (150 ml) and carefully extracted with 2N aqueous hydrochloric acid (4×25 ml). The aqueous acidic extracts were combined and basified with aqueous $NH_4OH$ with stirring at 0° C., giving a precipitate that was filtered off and dried under vaccum. The product was purified by HPLC. Yield: 1.2 g, 46%. MS: [M+1] 263.

Example 16
Purification and Culture of Retinal Ganglion Cells (RGC's)

RGCs from postnatal day 8 (P8) Sprague-Dawley rats were purified as previously described (Barres et al., 1988; Meyer-Franke et al., 1995). Purified retinal ganglion cells were plated onto tissue culture plastic precoated with poly-D-lysine and merosin, and cultured in serum-free Neurobasal medium (Gibco) containing various supplements.

A. Isolation of RGC's

The tissue from P8 Sprague/Dawley rat retinas (Simonsen Labs, CA) was dissociated enzymatically to obtain a suspension of single cells, by incubating the tissue in a papain solution (15 U/ml per retina, Worthington) in Earle's balanced salt solution (EBSS, Gibco) containing L-cysteine at 37° C. for an appropriate time to dissociate the tissue. The tissue was then disrupted sequentially with a 1 ml pipette, in a solution containing ovomucoid (Boehringer-Mannheim), DNase (Sigma), and bovine serum albumin (BSA; Sigma) to yield a single cell suspension. The cells were then washed in a suspension of ovomucoid/BSA.

B. Panning Procedure

Using sequential immunopanning, RGCs can be purified to greater than 99% homogeneity. Typically, 20–30% of the RGCs are isolated, which represents about 40,000 to 60,000 RGCs per P8 (post-natal, day 8) animal.

Panning plates were prepared in petri dishes (150 mm for the anti-rabbit IgG plates and 100 mm for the T11D7 plate) by incubating with Tris buffer solution (pH 9.5) containing 10 mg/ml of secondary antibody for approximately 12 hours at 4° C. Either affinity-purified goat anti-rabbit IgG (H+L chain-specific; Jackson Laboratories) or affinity-purified goat anti-mouse IgM (mu chain-specific; Jackson Laboratories) was used as the secondary antibody. The plates were then washed three times with phosphate-buffered saline (PBS), and the dish with anti-mouse IgM antibodies was further incubated with Thy 1.1 IgM monoclonal supernatant (antibody against mouse Thy 1.1, T11D7e2, ATCC, TIB 103) for approximately 2 hours at room temperature. After removing the supernatant, the plate was washed three times with PBS. To prevent non-specific binding of cells to the panning dish, PBS containing 2 mg/ml bovine serum albumin (BSA) was placed on the panning dishes.

The retinal cell suspension was incubated in anti-rat macrophage antiserum (Axell) for approximately 20 minutes, centrifuged, resuspended in PBS and incubated on an anti-rabbit panning plate for approximately 45 minutes. The plate was gently swirled every 15 minutes to ensure access of all cells to the surface of the plate. Following this, the cell suspension was transferred to a second anti-rabbit panning plate for approximately 30 minutes. Non-adherent cells were removed with the supernatant, filtered through a 15 $\mu$m Nytex mesh (Tetko) and placed on the T11D7 panning plate. After approximately 45 minutes, the plates were washed eight times with PBS to remove the non-adherent cells.

C. Removal of Adherent Cells

A trypsin solution (0.125%) was prepared by diluting a trypsin stock (Sigma) in EBSS ($Ca^{2+}$ and $Mg^{2+}$ free Eagle's balanced salt solution). The cells in the panning dish were incubated with 4 ml of this solution for ten minutes in a 5% $CO_2$ incubator. The cells were dislodged by gently pipetting the trypsin solution around the plate. Ten ml of 25% fetal calf serum medium was added to inactivate the trypsin, and the cells were centrifuged and resuspended in culture medium.

D. Culturing of RGC's

Approximately 5,000 purified RGCs were cultured in 96-well plates (Falcon), precoated with poly-D-lysine (PDL, 70 kD, 10 mg/ml; Sigma) and merosin (2 mg/ml; Gibco). The RGCs were cultured in serum-free Neurobasal medium (Brewer et al., 1993; Gibco) containing Sato-Bottenstein and B27 (Gibco) supplement, insulin (Sigma, 5 mg/ml), brain-derived neurotrophic factor (BDNF, 25 ng/ml; Preprotech), ciliary neurotrophic factor (CNTF, 20 ng/ml; Preprotech)

and forskolin (10 mM, Sigma). The percentage of surviving cells was assessed at 3, 7, and 14 days by the MTT assay.

Example 17
Oxygen/Glucose Deprivation (OGD) Model for Ischemia

Retinal ganglion cells were grown in 96-well plates for 5 days in serum-free medium as described above. On the sixth day cells were washed three times in a salt solution, e.g. Earle's balanced salt solution (EBSS, Gibco), containing glucose for control cells, and lacking glucose for test cells (oxygen/glucose-deprived cells). Control cells were further incubated in a 5% $CO_2$ incubator while OGD cells were deprived of oxygen in an anaerobic chamber (for 3 hours). Test compounds were added to control cells and OGD cells for the time period from 30 minutes prior to OGD, during OGD, and for 24 and 48 hours after OGD.

After 3 hours OGD, control and test cells were transferred to growth medium with glucose and cultured an additional 48 hours in a 5% $CO_2$ incubator, followed by a determination of cell viability using MTT, propidium iodide and annexin assays.

For the cell viability assay, MTT was added to culture and incubated at 37° C. for 1 hr. Viable cells with active mitochondria cleave the tetrazolium ring to form a visible dark blue formazan product. Viable and dead cells are counted by bright field microscopy at various times, e.g. 24, 48, or 72 hours after oxygen/glucose and/or growth factor deprivation. All values are reported as the mean (average) +/− the standard error of the mean (SEM) for at least three replicate cultures.

24 hours after oxygen/glucose deprivation (OGD), approximately 25% fewer retinal ganglion cells were determined to be alive relative to non-deprived control cells. After 48 hours, 40% fewer cells survived relative to non-deprived control cells. The dead cells showed the typical shrunken morphology of apoptotic cells. To confirm that the retinal ganglion cells died of programmed cell death (apoptosis) following OGD, cell cultures were labeled with FITC-coupled annexin V (ApoAlert Kit, Clonetech) and PI at 24 and 48 hours after OGD, followed by light and fluorescent microscopy. 200 cells were counted per triplicate value. The percentage of annexin positive cells was consistent with that of dead cells observed in previous experiments. Approximately 80% total dead RGCs were also annexin V positive at both 24 and 48 hours, indicating that the majority of cells died by apoptosis.

Example 18
in vivo Focal Ischemia Model

A. Rat Filament Model

Adult male Wistar rats weighing 310–380 g were used. Animals were fasted overnight but allowed free access to water. Anesthesia was induced and maintained with 3% isoflurane in 0.8% oxygen. Systemic blood pressure was recorded before, during and after middle cerebral artery occlusion (MCAO) and immediately before administering the test compound. Subjects received test compound SNX 912, 5 mg/kg ICV pre-MCAO, or 25 mg/kg IV immediately following reperfusion, after two hours MCAO, as compared to control subjects, which received deionized water. Temperature was controlled and recorded before, during and following reperfusion. After reperfusion, temperature was measured every hour for 4 hrs post-reperfusion.

All animals were subjected to 2 hr of MCAO using the intraluminal filament technique of Koizume et al. (1986) as modified by Zhao et al. (1994). A midline surgical incision was made to expose the right common, external and internal carotid arteries. The common cartotid, external and occipital arteries were tightly ligated, and the internal carotid artery was temporarily closed with a microvascular clip. A small incision was made in the common carotid artery and a nylon monofilament was inserted into the internal carotid artery through the common carotid artery. The filament was then carefully advanced 19 mm cephalad to occlude the middle cerebral artery at its site of origin within the Circle of Willis. Anesthesia was terminated, and upon awakening the animals were observed for the appearance of neurological deficits during MCAO. After 2 hr of MCAO, the animals were re-anesthetized with 1.5% halothane, and the occlude filament was withdrawn to allow reperfusion.

Because MCAO by the intraluminal filament technique can give rise to intra- and post-ischemia hyperthermia, rectal temperature was controlled by external heating and cooling for 6 hrs after initiating MCAO. Rectal temperature was maintained at 37.5+/−0.5° C.

B. Evaluation of Ischemic Damage Following MCAO

Animals were killed 24 hr post-reperfusion by $CO_2$ asphyxiation. Following asphyxiation, the brains were quickly removed and chilled in ice cold 0.9% saline for 10 min. To visualize the extent of ischemic damage, seven 2 mm thick coronal slices were cut from each brain with a tissue slicer beginning with 1 mm posterior to the anterior pole. The slices were immersed in a 0.9% saline solution containing 1.0% 2,3,5-tripheyltetrazolim chloride (TTC) and incubated at 37° C. for 30 minutes, and observed for the presence of formazan (red), which is produced by the reduction of TTC by endogenous dehydrogenase activity in normal living tissues.

What is claimed is:

1. A 4-amino-2-(benzimidazol-2'-yl)methyl compound having the structure Ia:

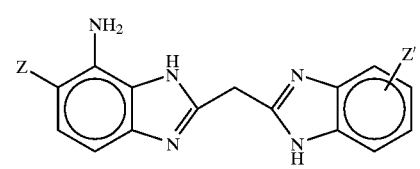

where Z' represents a 4' or 5' substituent on the rightmost depicted ring, and each of Z and Z' is independently selected from the group consisting of hydrogen, chloro, fluoro, carboxy, and methyl.

2. The compound of claim 1, where one of Z and Z' is hydrogen.

3. The compound of claim 1, where both Z and Z' are hydrogen, said compound being designated herein as SNX-912.

4. The compound of claim 2, where Z is hydrogen and Z' is 5'-chloro, said compound being designated herein as SNX-923.

5. The compound of claim 2, where Z' is hydrogen and Z is 5-chloro, said compound being designated herein as SNX-947.

6. The compound of claim 2, where Z is hydrogen and Z' is 4'-fluoro, said compound being designated herein as SNX-940.

7. The compound of claim 2, where Z is hydrogen and Z' is 5'-fluoro, said compound being designated herein as SNX-942.

8. The compound of claim 2, where Z is hydrogen and Z' is 5'-carboxy, said compound being designated herein as SNX-977.

9. The compound of claim 2, where Z is hydrogen and Z' is 4'-methyl, said compound being designated herein as SNX-944.

10. The compound 2,2-carbonylbisbenzimidazole, designated herein as SNX 1719.

11. A pharmaceutical composition useful for inhibiting cell death, comprising an effective amount of a compound of formula I, or a pharmaceutically acceptable salt thereof, in a pharmaceutically acceptable carrier:

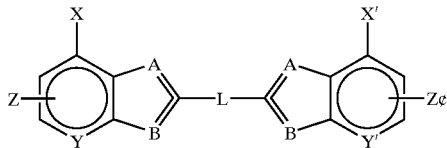

I where

X, X', Z and Z' are independently selected from the group consisting of hydrogen, alkyl, alkoxy, cyano, carboxylic acid or ester, sulfonic acid or ester, amino, alkylamino, nitro, and halogen, wherein at least one of X and X' is non-hydrogen;

L is $NR^1$, carbonyl, or $CR^2R^3$, where $R^1$ and $R^2$ are independently selected from hydrogen, alkyl, aryl, and aralkyl, and $R^3$ is selected from hydrogen, lower alkyl, amino, lower alkylamino, nitro, halogen, and lower alkyl sulfonate;

A===B represents a three-atom linkage effective to form an imidazole ring fused to the adjacent six-membered ring, where one of A and B is nitrogen and the other is $NR^1$, where A===B groups on opposing sides of the linker L may be the same or different;

Y is selected from C—Z and nitrogen, and Y' is selected from C-Z' and nitrogen.

12. The composition of claim 11, wherein L is $CH_2$.

13. The composition of claim 11, wherein $NR^1$ is NH, $NCH_3$, or $NCH_2C_6H_5$ (N-benzyl).

14. The composition of claim 11, wherein Y and Y' are C—Z and C—Z', respectively.

15. The composition of claim 11, wherein at least one of X and X' is amino or nitro.

16. The composition of claim 15, wherein X, X', Z and Z' are independently selected from hydrogen, alkyl, carboxylic acid or ester, amino, nitro, chloro, and fluoro.

17. The composition of claim 16, wherein Z and Z' are independently selected from hydrogen, carboxylic acid, chloro, and fluoro.

18. The composition of claim 13, wherein each $NR^1$ is $NCH_3$, L is $CHCH_3$, each of Y and Y' is CH, and each of Z, and Z' is hydrogen.

19. A pharmaceutical composition useful for inhibiting cell death, comprising an effective amount of the compound 2,2'-methylenebis(4-azabenzimidazole), designated herein as SNX911, or a pharmaceutically acceptable salt thereof, in a pharmaceutically acceptable carrier.

* * * * *